(12) United States Patent
Hyde et al.

(10) Patent No.: US 10,099,053 B2
(45) Date of Patent: Oct. 16, 2018

(54) EPIDERMAL ELECTRONICS TO MONITOR REPETITIVE STRESS INJURIES AND ARTHRITIS

(71) Applicant: Elwha LLC, Bellevue, WA (US)

(72) Inventors: Roderick A. Hyde, Redmond, WA (US); Jordin T. Kare, Seattle, WA (US); Eric C. Leuthardt, Louis, MO (US); Mark A. Malamud, Seattle, WA (US); Tony S. Pan, Bellevue, WA (US); Elizabeth A. Sweeney, Seattle, WA (US); Clarence T. Tegreene, Mercer Island, WA (US); Charles Whitmer, North Bend, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 631 days.

(21) Appl. No.: 14/504,954

(22) Filed: Oct. 2, 2014

(65) Prior Publication Data

US 2016/0015972 A1    Jan. 21, 2016

Related U.S. Application Data

(63) Continuation-in-part of application No. 14/334,434, filed on Jul. 17, 2014.

(51) Int. Cl.
*A61B 5/00* (2006.01)
*A61B 5/103* (2006.01)
(Continued)

(52) U.S. Cl.
CPC ........ *A61N 1/36014* (2013.01); *A61B 5/0022* (2013.01); *A61B 5/0488* (2013.01);
(Continued)

(58) Field of Classification Search
CPC ........ A61B 2018/00434; A61B 5/6831; A61B 5/4893; A61B 5/01; A61B 5/02438; A61B 5/0245; A61B 5/05
(Continued)

(56) References Cited

U.S. PATENT DOCUMENTS

| | | | | |
|---|---|---|---|---|
| 4,813,436 A | * | 3/1989 | Au | A61B 5/1038 356/620 |
| 5,131,401 A | * | 7/1992 | Westenskow | A61B 5/1106 600/554 |

(Continued)

OTHER PUBLICATIONS

Fleet, David J.; "Motion Models for People Tracking"; Visual Analysis of Humans; 2011; pp. 171-198; Springer-Verlag London Limited.
(Continued)

*Primary Examiner* — May Abouelela
(74) *Attorney, Agent, or Firm* — Daniel J. Honz; Advent, LLP

(57) ABSTRACT

Systems and methods are described for monitoring, treating, and preventing a repetitive stress injury, arthritis or other medical condition. A system embodiment includes, but is not limited to, a deformable substrate configured to interface with a skin surface; a sensor assembly coupled to the deformable substrate, the sensor assembly including a motion sensor and a physiological sensor, the sensor assembly configured to generate one or more sense signals based on detection of a movement of a body portion by the motion sensor and a physiological parameter of the body portion by the physiological sensor; a processor operably coupled to the sensor assembly and configured to receive the one or more sense signals; and an effector operably coupled to the processor and configured to affect the body portion responsive to control by the processor.

11 Claims, 31 Drawing Sheets

(51) Int. Cl.
   *A61N 1/36* (2006.01)
   *A61N 1/372* (2006.01)
   *A61N 1/378* (2006.01)
   *A61B 5/0488* (2006.01)
   *A61B 5/11* (2006.01)
   *H02J 7/02* (2016.01)
   *H02J 50/10* (2016.01)
   *G16H 50/30* (2018.01)
   *G06F 19/00* (2018.01)
   *H02J 50/12* (2016.01)

(52) U.S. Cl.
   CPC .......... *A61B 5/1116* (2013.01); *A61B 5/1121* (2013.01); *A61B 5/1127* (2013.01); *A61B 5/459* (2013.01); *A61B 5/4528* (2013.01); *A61B 5/4585* (2013.01); *A61B 5/7275* (2013.01); *A61B 5/7282* (2013.01); *A61B 5/7455* (2013.01); *A61N 1/3787* (2013.01); *A61N 1/37247* (2013.01); *A61N 1/37282* (2013.01); *G06F 19/00* (2013.01); *G16H 50/30* (2018.01); *H02J 7/025* (2013.01); *H02J 50/10* (2016.02); *A61B 5/1125* (2013.01); *A61B 5/4514* (2013.01); *A61B 2503/08* (2013.01); *A61B 2560/0214* (2013.01); *A61B 2562/0219* (2013.01); *A61N 1/36003* (2013.01); *H02J 50/12* (2016.02)

(58) Field of Classification Search
   USPC ................... 600/300, 301, 587, 595; 607/62
   See application file for complete search history.

(56) References Cited

U.S. PATENT DOCUMENTS

| | | | |
|---|---|---|---|
| 5,215,100 A | 6/1993 | Spitz et al. | |
| 5,792,025 A | 8/1998 | Kikinis | |
| 5,860,939 A * | 1/1999 | Wofford | A61B 5/0484 600/547 |
| 5,924,999 A | 7/1999 | Agee et al. | |
| 5,941,836 A * | 8/1999 | Friedman | A61B 5/1116 200/61.45 R |
| 6,142,910 A | 11/2000 | Heuvelman | |
| 7,383,071 B1 | 6/2008 | Russell et al. | |
| 8,057,388 B1 | 11/2011 | Russell et al. | |
| 8,111,165 B2 | 2/2012 | Ortega et al. | |
| 8,416,088 B2 | 4/2013 | Ortega et al. | |
| 2003/0236458 A1 | 12/2003 | Hochman | |
| 2004/0133081 A1 * | 7/2004 | Teller | A61B 5/01 600/300 |
| 2004/0225211 A1 | 11/2004 | Gozani et al. | |
| 2007/0055176 A1 | 3/2007 | Branch et al. | |
| 2008/0300650 A1 * | 12/2008 | Gerber | A61B 5/202 607/41 |
| 2009/0036799 A1 * | 2/2009 | Sandhu | A61B 5/0476 600/587 |
| 2009/0076418 A1 | 3/2009 | Jung et al. | |
| 2010/0002402 A1 | 1/2010 | Rogers et al. | |
| 2010/0228315 A1 * | 9/2010 | Nielsen | A61B 5/0215 607/42 |
| 2010/0249532 A1 * | 9/2010 | Maddess | A61B 3/024 600/300 |
| 2011/0118698 A1 | 5/2011 | Eckhoff et al. | |
| 2011/0230745 A1 | 9/2011 | Chandrasekaran et al. | |
| 2012/0053890 A1 | 3/2012 | Van Acht et al. | |
| 2012/0071731 A1 * | 3/2012 | Gottesman | A61B 5/486 600/301 |
| 2012/0108999 A1 * | 5/2012 | Leininger | A61B 5/0004 600/546 |
| 2012/0143023 A1 * | 6/2012 | Costantino | A61B 5/1107 600/309 |
| 2012/0157804 A1 | 6/2012 | Rogers et al. | |
| 2012/0165759 A1 | 6/2012 | Rogers et al. | |
| 2013/0041235 A1 | 2/2013 | Rogers et al. | |
| 2013/0192071 A1 | 8/2013 | Esposito et al. | |
| 2013/0245486 A1 * | 9/2013 | Simon | A61N 1/36021 600/546 |
| 2014/0005494 A1 * | 1/2014 | Ternes | A61B 5/0028 600/300 |
| 2014/0070957 A1 | 3/2014 | Longinotti-buitoni et al. | |
| 2014/0206945 A1 * | 7/2014 | Liao | A61N 1/0529 600/301 |
| 2014/0275821 A1 | 9/2014 | Beckman | |
| 2014/0296749 A1 * | 10/2014 | Reid, Jr. | A61B 5/0053 600/587 |
| 2014/0371547 A1 * | 12/2014 | Gartenberg | A61B 5/0048 600/301 |
| 2015/0072326 A1 * | 3/2015 | Mauri | A61B 5/0488 434/247 |
| 2015/0080670 A1 * | 3/2015 | Osorio | A61B 5/0205 600/301 |
| 2015/0142079 A1 * | 5/2015 | Pensler | A61N 1/36003 607/48 |
| 2015/0224326 A1 * | 8/2015 | Toth | A61B 5/042 600/301 |
| 2015/0238259 A1 * | 8/2015 | Albeck | A61B 18/22 606/3 |
| 2016/0022167 A1 * | 1/2016 | Simon | A61B 5/04842 600/301 |
| 2016/0106344 A1 | 4/2016 | Nazari | |
| 2016/0143536 A1 | 5/2016 | Hyde et al. | |

OTHER PUBLICATIONS

Joao Luis Marins, Xiaoping Yun, Eric R. Bachmann, Robert B. McGhee, and Michael J. Zyda; An Extended Kalman Filter for Quaternion-Based Orientation Estimation Using MARG Sensors; Proceedings of the 2001 IEEE/RSJ International Conference on Intelligent Robots and Systems, Maui, Hawaii; Oct. 29-Nov. 3, 2001; pp. 2003-2011.

Wei-Zhong Wang, Bang-Yu Huang, Lei Wang; Analysis of Filtering Methods for 3D Acceleration Signals in Body Sensor Network; Bulletin of Advanced Technology Research; vol. 5, No. 7; Jul. 2011; pp. 15-18.

Xiaoping Yun and Eric R. Bachmann; Design, Implementation, and Experimental Results of a Quaternion-Based Kalman Filter for Human Body Motion Tracking; IEEE Transactions on Robotics; vol. 22, No. 6; Dec. 2006; pp. 1216-1227.

Dae-Hyeong Kin, Nanshu Lu, Rui Ma, Yun-Soung Kim, Rak-Hwan Kim, Shuodao Wang, Jian Wu, Sang Min Won, Hu Tao, Ahmad Islam, Ki Jun Yu, Tae-Il Kim, Raeed Chowdhury, Ming Ying, Lizhi Su, Ming Li, Hyun-Joong Chung, Hohyun Keum, Martin McCormick, Ping Liu, Yong-Wei Zhang, Fiorenze G. Omenetoo, Yonggang Huang, Todd Coleman, John A. Rogers; Epidermal Electronics; www.sciengemag.org; Aug. 12, 2011, Corrected Sep. 23, 2011; vol. 333; pp. 838-843.

Woon-Hong Yeo, Yun-Soung Kim, Jongwoo Lee, Abid Ameen, Luke Shi, Ming Li, Shuodao Wang, Rui Ma, Sung Hun Jin, Zhan Kang, Yonggang Huang, and John A. Rogers; Multifuncational Epidermal Electronics Printed Directly Onto the Skin; Adv. Mater.; 2013; pp. 1-6.

Sheng Yu, Yihui Zhang, Lin Jia, Kyle E. Mathewson, Kyung-In Jang, Jeonghyun Kim, Haoran Fu, Xian Huang, Pranav Chava, Renhan Wang, Sanat Bhole, Lizhe Wang, Yoon Joo Na, Yue Guan, Matthew Flavin, Zheshen Hand, Yonggang Huang, John A. Rogers; Soft Microfluidic Assemblies or Sensors, Circuits, and Radios for the Skin; Science; Apr. 4, 2014; vol. 344; pp. 70-74.

Ming Ying, Andrew P. Bonifas, Nanshu Lu, Yewang Su, Rui Li, Huanyu Cheng, Abid Ameen, Yonggang Huang and John A. Rogers; Silicon nanomembranes for fingertip electronics; Nanotechnology; 2012; No. 23; pp. 1-11.

R. Chad Webb, Andrew P. Bonifas, Alex Behnaz, Yihui Zhang, Ki Jun Yu, Huanyu Cheng, Mingxing Shi, Zuguang Bian, Zhuangjian Liu, Yun-Soung Kim, Woon-Hong Yeo, Jae Suk Park, Jizhou Song, Yuhang Li, Yonggang Huang, Alexander M. Gorbach, and John A. Rogers; Ultrathin conformal devices for precise and continuous

(56) References Cited

OTHER PUBLICATIONS thermal characterization of human skin; Nature Materials; Oct. 2013; vol. 12; pp. 938-945, supplemental information pp. 1-27.
Donghee Son, Jongha Lee, Shutao Qiao, Roozbeh Ghaffari, Jaemin Kim, Ji Eun Lee, Changyeong Song, Seok Joo Kim, Dong Jun Lee, Samuel Woojoo Jun, Shixuan Yang, Minjoon Park, Jiho Shin, Kyungsik Do, Mincheol Lee, Kwanghun Kang, Cheol Seong Hwang, Nanshu Lu, Taeghwan Hyeon and Dae-Hyeong Kim; Multifunctional wearable devices for diagnosis and therapy of movement disorders; Nature Nanotechnology; Mar. 30, 2014; pp. 1-8.
Lei Sun, Guoxuan Qin, Jung-Hun Seo, George K. Celler, Weidong Zhou, and Zhenqiang Ma; 12-GHz Thin-Film Transistors on Transferrable Silicon Nanomembranes for High-Performance Flexible Electronics; small; 2010; vol. 6, No. 22; pp. 2553-2557.
F. Axisa, D. Brosteaux, E. De Leersnyder, F. Bossuyt, J. Vanfleteren, B. Hermans, R. Puers; Biomedical Strectchable Systems Using Mid Based Stretchable Electronics Technology; Proceedings of the 29th Annual International Conference on the IEEE EMBS Cite International, Lyon France; Aug. 23-26, 2007; pp. 5687-5690.
Keith T. Palmer; Carpal tunnel syndrome; The role of occupational factors; pp. 1-12.
PCT International Search Report; International App. No. PCT/2017/066611; dated Mar. 30, 2018; pp. 1-5.

\* cited by examiner

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

> 1900 COMPARING THE ONE OR MORE SENSE SIGNALS TO REFERENCE DATA INDICATIVE OF A STRAIN INJURY TO DETERMINE THE RISK OF INDUCING THE STRAIN INJURY
>
> > 1902 DETERMINING THE ACTION TO EXECUTE BASED UPON COMPARING THE ONE OR MORE SENSE SIGNALS TO REFERENCE DATA INDICATIVE OF A STRAIN INJURY

1808 EXECUTING AN ACTION TO REDUCE THE RISK OF INDUCING THE REPETITIVE STRESS INJURY

FIG. 18

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2000 REPORTING THE DETERMINATION OF THE RISK OF INDUCING THE REPETITIVE STRAIN INJURY TO REDUCE THE RISK

2002 PROVIDING A TACTILE INDICATION OF THE RISK

2004 PROVIDING A VIBRATION-BASED INDICATION OF THE RISK

2006 PROVIDING A TACTILE INDICATION REGARDING A POSITION OF THE BODY PORTION

2008 PROVIDING A TACTILE INDICATION THAT THE POSITION IS A BIOMECHANICALLY DETRIMENTAL POSITION

2010 PROVIDING A TACTILE INDICATION THAT THE BODY PORTION HAS BEEN IN THE POSITION LONGER THAN A THRESHOLD DURATION

FIG. 19

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2000 REPORTING THE DETERMINATION OF THE RISK OF INDUCING THE REPETITIVE STRAIN INJURY TO REDUCE THE RISK

2100 PROVIDING A VISUAL INDICATION OF THE RISK

2102 PROVIDING A VISUAL INDICATION REGARDING A POSITION OF THE BODY PORTION

2104 PROVIDING A VISUAL INDICATION THAT THE POSITION IS A BIOMECHANICALLY DETRIMENTAL POSITION

2106 PROVIDING A VISUAL INDICATION THAT THE BODY PORTION HAS BEEN IN THE POSITION LONGER THAN A THRESHOLD DURATION

FIG. 20

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2000 REPORTING THE DETERMINATION OF THE RISK OF INDUCING THE REPETITIVE STRAIN INJURY TO REDUCE THE RISK

2200 PROVIDING AN AUDITORY INDICATION OF THE RISK

2202 PROVIDING AN AUDITORY INDICATION REGARDING A POSITION OF THE BODY PORTION

2204 PROVIDING AN AUDITORY INDICATION THAT THE POSITION IS A BIOMECHANICALLY DETRIMENTAL POSITION

2206 PROVIDING AN AUDITORY INDICATION THAT THE BODY PORTION HAS BEEN IN THE POSITION LONGER THAN A THRESHOLD DURATION

FIG. 21

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2000 REPORTING THE DETERMINATION OF THE RISK OF INDUCING THE REPETITIVE STRAIN INJURY TO REDUCE THE RISK

2300 REPORTING AT LEAST ONE OF AN ACTUATION OF AN EFFECTOR CONFIGURED TO EXECUTE THE ACTION, A DETECTED MOVEMENT OF THE BODY PORTION, OR A DETECTED PHYSIOLOGICAL CONDITION

2302 PROVIDING A WARNING OF A RISK OF A BIOMECHANICALLY DETRIMENTAL POSITIONING OF THE BODY PORTION

2304 PROVIDING AN INSTRUCTION TO MOVE THE BODY PORTION

2306 COMMUNICATING THE DETERMINATION TO A REMOTE LOCATION

2308 INTERACTING WITH A PROGRAM STORED ON THE COMPUTER SYSTEM

2310 MODIFYING A PROGRAM STORED ON THE COMPUTER SYSTEM

FIG. 22

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

> 2400 STIMULATING A NERVE PROXIMATE TO THE BODY PORTION
>
>> 2402 INDUCING AT LEAST ONE OF A MOVEMENT OR A SENSATION OF THE BODY PORTION BY STIMULATING THE NERVE CONDUCTION OF THE NERVE PROXIMATE TO THE BODY PORTION
>>
>>> 2404 INDUCING AT LEAST ONE OF A MOVEMENT OR A SENSATION OF THE BODY PORTION BY STIMULATING A NERVE CONDUCTION OF THE NERVE AFTER A THRESHOLD PERIOD OF TIME DURING WHICH THE BODY PORTION IS RETAINED IN A PARTICULAR POSITION

FIG. 23

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

> 2500 ELECTRICALLY BLOCKING A NERVE CONDUCTION OF A NERVE PROXIMATE TO THE BODY PORTION
>
> > 2502 ELECTRICALLY BLOCKING A NERVE CONDUCTION OF A NERVE PROXIMATE TO THE BODY PORTION TO INHIBIT A PAIN RECEPTOR
> >
> > 2504 ELECTRICALLY BLOCKING A NERVE CONDUCTION OF A NERVE PROXIMATE TO THE BODY PORTION TO INHIBIT A MOVEMENT OF THE BODY PORTION

FIG. 24

1802 DETECTING, VIA AN EPIDERMAL ELECTRONIC SYSTEM (EES), AT LEAST ONE OF A POSITION AND A MOVEMENT OF A BODY PORTION

2600 MEASURING, VIA AN EPIDERMAL ELECTRONIC SYSTEM (EES), A REPEATED MOTION OF THE BODY PORTION

2602 MEASURING, VIA AN EPIDERMAL ELECTRONIC SYSTEM (EES), A NUMBER OF REPETITIONS OF THE MOVEMENT OF THE BODY PORTION

2604 MEASURING, VIA AN EPIDERMAL ELECTRONIC SYSTEM (EES), A SPEED OF THE MOVEMENT OF THE BODY PORTION

2606 MEASURING, VIA AN EPIDERMAL ELECTRONIC SYSTEM (EES), A DURATION OF THE MOVEMENT OF THE BODY PORTION

2608 MEASURING, VIA AN EPIDERMAL ELECTRONIC SYSTEM (EES), A DISPOSITION OF THE BODY PORTION RELATIVE TO A SECOND BODY PORTION

2610 MEASURING, VIA AN EPIDERMAL ELECTRONIC SYSTEM (EES), AN ANGLE OF MOVEMENT OF THE BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

FIG. 25

1802  DETECTING, VIA AN EPIDERMAL ELECTRONIC SYSTEM (EES), AT LEAST ONE OF A POSITION AND A MOVEMENT OF A BODY PORTION

1804  GENERATING ONE OR MORE SENSE SIGNALS BASED ON DETECTION OF THE AT LEAST ONE OF A POSITION AND A MOVEMENT OF A BODY PORTION

1806  PROCESSING THE ONE OR MORE SENSE SIGNALS TO DETERMINE A RISK OF INDUCING A REPETITIVE STRESS INJURY

1808  EXECUTING AN ACTION TO REDUCE THE RISK OF INDUCING THE REPETITIVE STRESS INJURY

2700  DETECTING, VIA AN EPIDERMAL ELECTRONIC SYSTEM (EES), A PHYSIOLOGICAL PARAMETER OF THE BODY PORTION

2702  GENERATING ONE OR MORE SENSE SIGNALS BASED ON DETECTION OF THE PHYSIOLOGICAL PARAMETER OF THE BODY PORTION

FIG. 26

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2700 DETECTING, VIA AN EPIDERMAL ELECTRONIC SYSTEM (EES), A PHYSIOLOGICAL PARAMETER OF THE BODY PORTION

2800 DETECTING A TEMPERATURE OF THE BODY PORTION

2802 DETECTING A STRAIN OF THE BODY PORTION

2804 DETECTING A BLOOD FLOW OF THE BODY PORTION

2806 DETECTING A BLOOD OXYGENATION LEVEL OF THE BODY PORTION

2808 DETECTING AN ELECTRICAL ACTIVITY OF THE BODY PORTION

2702 GENERATING ONE OR MORE SENSE SIGNALS BASED ON DETECTION OF THE PHYSIOLOGICAL PARAMETER OF THE BODY PORTION

FIG. 27

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2900 DETECTING, VIA AN EPIDERMAL ELECTRONIC SYSTEM (EES), A DISPOSITION OF THE BODY PORTION

2902 DETECTING, VIA AN EPIDERMAL ELECTRONIC SYSTEM (EES), AN ANGLE OF A JOINT PROXIMATE THE BODY PORTION

2904 DETECTING, VIA AN EPIDERMAL ELECTRONIC SYSTEM (EES), A DISPOSITION OF THE BODY PORTION OVER A PERIOD OF TIME

FIG. 28

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

3000 DETECTING, VIA AN EPIDERMAL ELECTRONIC SYSTEM (EES), A DEVICE INTERFACING WITH AT LEAST ONE OF THE BODY PORTION AND ANOTHER BODY PORTION

3002 TRANSMITTING A COMMUNICATION SIGNAL TO THE DEVICE

3004 TRANSMITTING THE ONE OR MORE SENSE SIGNALS GENERATED BASED ON DETECTION OF AT LEAST ONE OF THE POSITION AND THE MOVEMENT OF THE BODY PORTION TO THE DEVICE

FIG. 29

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

3100 DETECTING, VIA AN EPIDERMAL ELECTRONIC SYSTEM (EES), AT LEAST ONE OF A POSITION AND A MOVEMENT OF A SECOND BODY PORTION PROXIMATE THE BODY PORTION

FIG. 30

EPIDERMAL ELECTRONICS TO MONITOR REPETITIVE STRESS INJURIES AND ARTHRITIS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 14/334,434, entitled USE OF EPIDERMAL ELECTRONIC DEVICES TO MEASURE ORIENTATION, naming ALISTAIR K. CHAN, RODERICK A. HYDE, ELIZABETH A. SWEENEY, and DAVID B. TUCKERMAN as inventors, filed 17 Jul. 2014, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system includes, but is not limited to, a deformable substrate configured to interface with a skin surface; a sensor assembly coupled to the deformable substrate, the sensor assembly including a motion sensor and a physiological sensor, the sensor assembly configured to generate one or more sense signals based on detection of a movement of a body portion by the motion sensor and a physiological parameter of the body portion by the physiological sensor; a processor operably coupled to the sensor assembly and configured to receive the one or more sense signals; and an effector operably coupled to the processor and configured to affect the body portion responsive to control by the processor.

In an aspect, a system includes, but is not limited to a first system, a second system, and a communications interface between the first system and the second system. The first system includes, but is not limited to, a deformable substrate configured to interface with a skin surface; a sensor assembly coupled to the deformable substrate, the sensor assembly including a motion sensor and a physiological sensor, the sensor assembly configured to generate one or more sense signals based on detection of a movement of a body portion by the motion sensor and a physiological parameter of the body portion by the physiological sensor; a processor operably coupled to the sensor assembly and configured to receive the one or more sense signals; and an effector operably coupled to the processor and configured to affect the body portion responsive to control by the processor. The second system includes, but is not limited to, a second deformable substrate configured to interface with a second skin surface; a second sensor assembly coupled to the second deformable substrate, the second sensor assembly including a motion sensor and a physiological sensor, the second sensor assembly configured to generate one or more sense signals based on detection of a movement of a second body portion by the motion sensor of the second sensor assembly and a physiological parameter of the second body portion by the physiological sensor of the second sensor assembly; a second processor operably coupled to the second sensor assembly and configured to receive the one or more sense signals of the second sensor assembly; and a second effector operably coupled to the second processor and configured to affect the second body portion responsive to control by the second processor.

In an aspect, a method includes, but is not limited to, detecting, via an epidermal electronic system (EES), at least one of a position and a movement of a body portion; generating one or more sense signals based on detection of the at least one of a position and a movement of a body portion; processing the one or more sense signals to determine a risk of inducing a repetitive stress injury; and executing an action to reduce the risk of inducing the repetitive stress injury.

In an aspect, a computer-implemented method includes, but is not limited to, receiving, by a computer processor, one or more sense signals based on detection of at least one of a position and a movement of a body portion; processing, by the computer processor, the one or more sense signals to determine a risk of inducing a repetitive stress injury; and controlling, by the computer processor, an effector positioned on the body portion to execute an action to reduce the risk of inducing the repetitive stress injury.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 18 is a flowchart illustrating aspects of a method such as shown in FIG. 17.

FIG. 19 is a flowchart illustrating aspects of a method such as shown in FIG. 17.

FIG. 20 is a flowchart illustrating aspects of a method such as shown in FIG. 19.

FIG. 21 is a flowchart illustrating aspects of a method such as shown in FIG. 19.

FIG. 22 is a flowchart illustrating aspects of a method such as shown in FIG. 19.

FIG. 23 is a flowchart illustrating aspects of a method such as shown in FIG. 17.

FIG. 24 is a flowchart illustrating aspects of a method such as shown in FIG. 17.

FIG. 25 is a flowchart illustrating aspects of a method such as shown in FIG. 17.

FIG. 26 is a flowchart illustrating aspects of a method such as shown in FIG. 17.

FIG. 27 is a flowchart illustrating aspects of a method such as shown in FIG. 26.

FIG. 28 is a flowchart illustrating aspects of a method such as shown in FIG. 17.

FIG. 29 is a flowchart illustrating aspects of a method such as shown in FIG. 17.

FIG. 30 is a flowchart illustrating aspects of a method such as shown in FIG. 17.

DETAILED DESCRIPTION

Figure 1A:
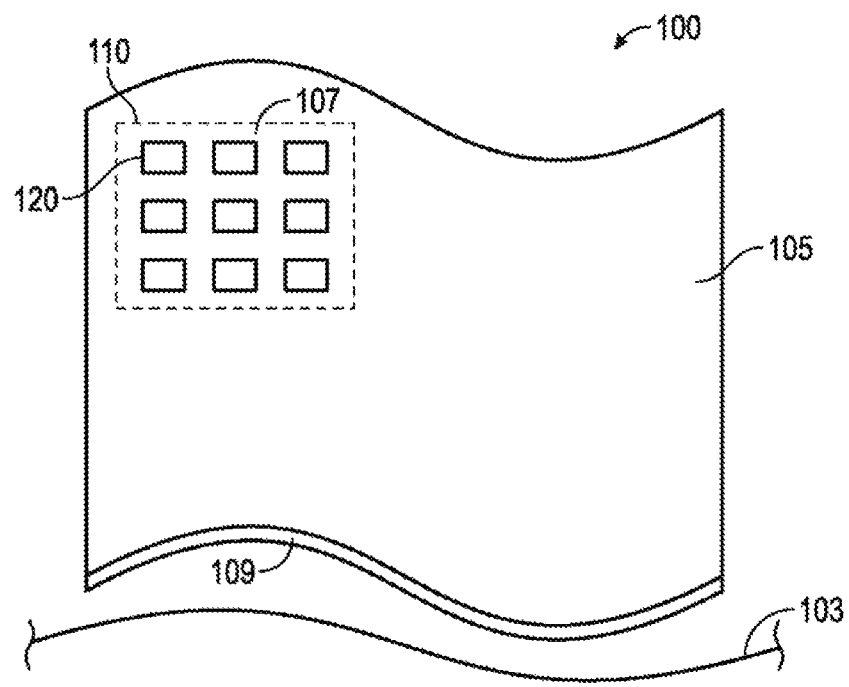
FIG. 1A is a schematic view of an embodiment of an epidermal electronics device showing individual cells of the device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, an epidermal electronics device may include a thin layer of electronic circuits. This thin layer is supported by a barrier layer and optionally encapsulated by a substrate layer. The device is configured to attach to skin or other tissue. The device is also configured to allow the electronic circuits to flex without being damaged. The epidermal electronics device includes electronics for measuring various parameters. In general, an epidermal electronics device may be used for a variety of medical applications.

Referring to FIG. 1A, an embodiment of epidermal electronics device 100 is shown to include substrate layer 105. Epidermal electronics device 100 further includes electronics layer 107 located between substrate layer 105 and barrier layer 109. Electronics layer 107 is shown through substrate layer 105 with view 110. Included within electronics layer 107 are cells 120. Epidermal electronics device 100 is illustrated as attached to attachment surface 103.

Substrate layer 105 facilitates the transfer of epidermal electronics device 100 to attachment surface 103. For example, substrate layer 105 may provide a backing which is used to transfer electronics layer 107 to attachment surface 103. Substrate layer 105 may then peel away from electronics layer 107 leaving electronics layer 107 attached to attachment surface 103 via barrier layer 109. Substrate layer 107 may also provide protection to electronics layer 107 during the handling of epidermal electronics device 100. Substrate layer 105 also provides support for electronics layer 107. Barrier layer 109 can be an elastomer or polymer suited for use in contact with organic tissue. In some embodiments, the barrier layer 109 is a bio compatible or otherwise inert material. In some embodiments, barrier layer 109 may have a low elastic modulus, e.g., one which is significantly lower (e.g., less than half) of the elastic modulus of attachment surface 103. For example, barrier layer 109 may comprise a low modulus polymeric material such as PDMS or BASF. For example, the substrate layer 105 may be a rubber or silicone material. In some embodiments, substrate layer 105 may be water soluble. Substrate layer 105 may be dissolved following transfer of the epidermal electronics device 100 onto the attachment surface 103. In some embodiments, substrate layer 105 need not be biocompatible as it is removed completely or partially following the transfer of epidermal electronics device 100 onto the attachment surface 103. Substrate layer 105 provides protection to electronics layer 107 from external sources of damage. External sources of damage may include moisture, physical damage (e.g., from a user touching epidermal electronics device 100), electrical interference, magnetic interference, etc.

In one embodiment, attachment surface 103 is the skin of a user. In other embodiments, attachment surface 103 includes other organs. For example, attachment surface 103 may be bone, muscle tissue, the heart, the lungs, etc. In some embodiments, attachment surface 103 is a bandage attached or to be attached to the skin or other organ.

Epidermal electronics device 100 is held in contact with attachment surface 103 through conformal contact. In some embodiments, epidermal electronics device 100 is held in contact with attachment surface 103 through close-contact atomic forces or van der Waals interactions. In other embodiments, epidermal electronics device 100 is held in contact with attachment surface 103 through the use of an adhesive. The adhesive may be applied after the epidermal electronics device 100 is placed on attachment surface 103. For example, the adhesive may be a spray on bandage or may be adhesive tape. The adhesive may also be included as a component of barrier layer 109.

According to one embodiment, barrier layer 109 at least partially encompasses the electronics layer 107. In some embodiments, barrier layer 109 encompasses the entirety of epidermal electronics layer 107. In other embodiments, barrier layer 109 only coats electronics layer 107 on the surface opposite substrate layer 105. Barrier layer 109 may also partially coat electronics layer 107 to allow for contact between elements or cells of electronics layer 107 and the attachment surface 103.

With continued reference to FIG. 1A, electronics layer 107 is located between substrate layer 105 and barrier layer 109. Barrier layer 109 and/or substrate layer 105 provides support for the elements of electronics layer 107. View 110, illustrated as a dashed line, shows electronics layer 107 through substrate layer 105. In one embodiment, electronics layer 107 includes an array of cells 120. Cells 120 contain individual sensors or components. Cells 120 are also in communication with other components in electronics layer 107. In some embodiments, cells 120 may be in communication with each other or a subset of other cells 120 within epidermal electronics device 100. Cells 120 may also be in communication with other elements. For example, cells 120 may be in communication with a power supply, control circuit, and/or communications device. Cells 120 may also contain connections to allow power delivery to the component in the cell, input/output to and from the component in the cell, and/or multiplexing circuitry. In some embodiments, cells 120 may contain sensors such as accelerometers, inclinometers, magnetometers, or gyroscopes. These sensors may be of the micro electro-mechanical systems (MEMS) type given the small scale of epidermal electronics device 100 and associated components; MEMS accelerometers, gyroscopes, and inclinometers are commercially available from multiple vendors. The sensors may also be part of or supported by integrated circuits or systems on a chip (SOCs). Cells 120 may also contain interaction devices such as drug delivery systems, electrodes, motion capture markers, etc. Interaction devices may also be MEMS, part of or supported by integrated circuits, or SOCs. According to various alternative embodiments, cells 120 may include circuitry facilitating multiplexing of sensor output, transformers, amplifiers, circuitry for processing data and control signals, one or more transistors, etc.

Figure 1B:
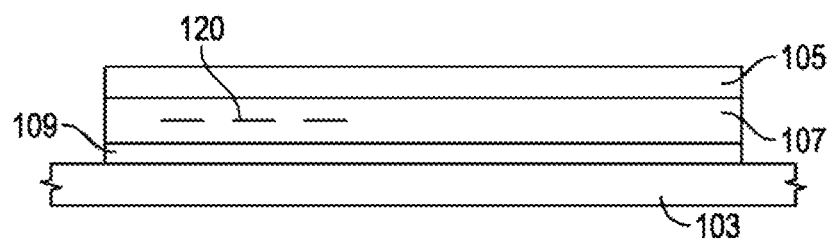
FIG. 1B is a schematic cross section view of an embodiment of an epidermal electronics device showing individual cells of the device.

FIG. 1B illustrates a cross section schematic view of one embodiment of epidermal electronics device 100. Substrate layer 105 is the topmost layer relative to attachment surface 103 and protects electronics layer 107 from the external environment. Barrier layer 109 is in contact with attachment surface 103 and protects electronics layer 107 from attachment surface 103. Electronics layer 107 is between barrier layer 109 and substrate layer 105. Electronics layer 107 is shown with cells 120 located therein.

As previously discussed, attachment surface 103 may be the skin of a user. Barrier layer 109 attaches epidermal electronics device 100 to attachment surface 103. Barrier layer 109 also protects electronic components of epidermal electronics device 100 from damage caused by attachment surface 103. Electronics layer 107, which includes electronic components of epidermal electronics device 100, is coupled to barrier layer 109. Lastly, substrate layer 105 is coupled to electronics layer 107. Substrate layer 105 may provide a surface on which epidermal electronics device 100 is constructed, further protects the electronics components of epidermal electronics device 100, and/or facilitates the attachment of epidermal electronics device 100 to attachment surface 103 (e.g., provides a peel away surface which may be grasped while attaching epidermal electronics device 100.

In alternative embodiments, epidermal electronics device may include a subset of the layers described above. For example, epidermal electronics device 100 may include only barrier layer 109 and the electronic components described herein. Barrier layer 109 may protect the electronic components, attach epidermal electronics device 100 to attachment surface 103, and provide a surface on which epidermal electronics device 100 is constructed. Substrate layer 105 is an optional component of epidermal electronics device 100.

Figure 2A:
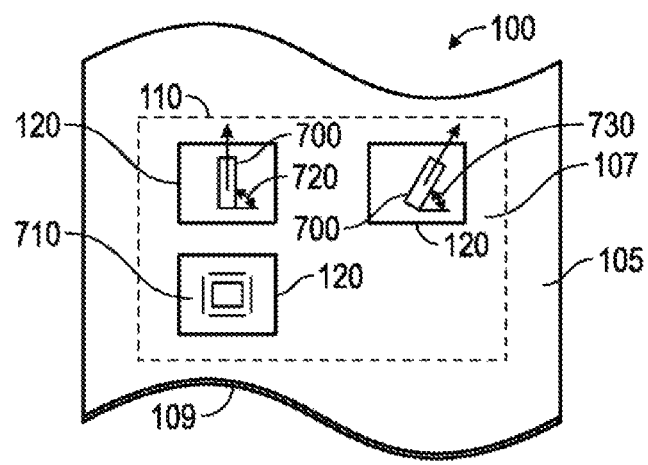
FIG. 2A is a schematic view of an embodiment of an epidermal electronics device showing cells configured to measure orientation using accelerometers.

FIG. 2A illustrates a schematic view of a portion of epidermal electronics device 100 according to one embodiment and shows sensors and sensor combinations which may be used. In some embodiments, epidermal electronics device 100 includes one or more single-axis accelerometers 700. Each accelerometer is located within one of cells 120. Single-axis accelerometers 700 may be positioned at angles such as first angle 720 and second angle 730. Some embodiments of epidermal electronics device 100 include multi-axis accelerometer 710.

In one embodiment, epidermal electronics device 100 includes two or more single-axis accelerometers 700. Each accelerometer is part of a single cell 120. Cell 120 facilitates communication between the single-axis accelerometer 700 and other components of the electronics layer 107. Cell 120 may include one or more transistors. As is shown with view 110, illustrated with a dashed line, the single-axis accelerometers 700 are part of electronics layer 107. Single-axis accelerometer 700 is a MEMS accelerometer measuring acceleration along a single axis. One single-axis accelerometer 700 is shown oriented at a first angle 720. Another single-axis accelerometer 700 is shown oriented at a second angle 730. By orienting two single-axis accelerometers at different angles, 720 and 730, the rotation and orientation of the epidermal electronics device 100 may be determined from the sensor outputs. The different angles 720 and 730 may result in the single-axis accelerometers being oriented along different planes. The single-axis accelerometers may be slightly or fully opposed. Some embodiments of the epidermal electronics device 100 include multi-axis accelerometer 710.

Figure 2B:
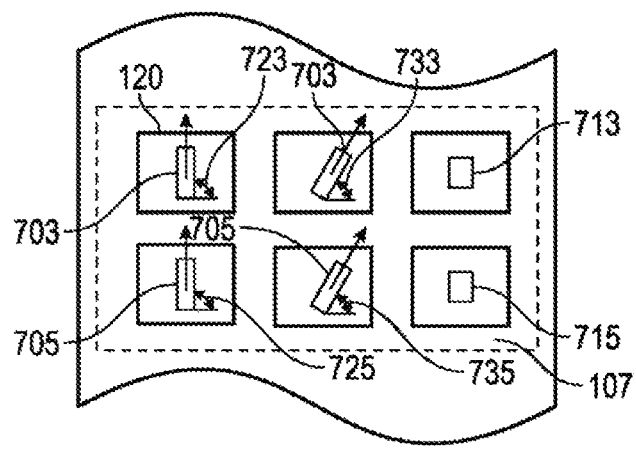
FIG. 2B is a schematic view of an embodiment of the epidermal electronics device showing cells configured to measure orientation using inclinometers and/or gyroscopes.

FIG. 2B illustrates additional sensors which may be included in an embodiment of epidermal electronics device 100. These additional sensors may include one or more of single-axis inclinometers 703, multi-axis inclinometers 713, single-axis gyroscopes 705, and multi-axis gyroscopes 715.

Inclinometers may be used to measure an orientation of epidermal electronics device 100 relative to the direction of gravity. One single-axis inclinometer 703 may be oriented at first angle 723. Another single-axis inclinometer 703 may be oriented at second angle 733. By orienting two single-axis inclinometers at different angles, 723 and 733, two components of the orientation of epidermal electronics device 100 relative to the direction of gravity may be determined from the sensor outputs. The different angles 720 and 730 may result in the single-axis inclinometers being oriented along different axes. Single-axis inclinometers may be used to measure pitch or roll relative to the direction of gravity. Some embodiments of epidermal electronics device 100 include a multi-axis inclinometer 713, i.e., to measure both pitch and roll. In some embodiments, electronics layer 107 includes one or more gyroscopes to measure an angular velocity of epidermal electronics device 100. In some embodiments, electronics layer 107 includes one or more single-axis gyroscopes 705 (e.g., a MEMS vibrating structure gyroscope). One single-axis gyroscope 705 may be oriented at first angle 725. Another single-axis gyroscope 705 may be oriented at second angle 735. By orienting two single-axis gyroscopes at different angles, 725 and 735, two components of the angular velocity of epidermal electronics device 100 may be determined from the sensor outputs. The different angles 725 and 735 may result in the single-axis inclinometers being oriented along different axes. Single-axis gyroscopes may be used to measure pitch, roll, and/or yaw. Some embodiments of epidermal electronics device 100 include a multi-axis gyroscope 715.

Figure 2C:
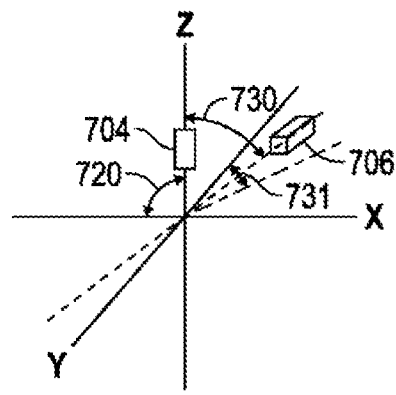
FIG. 2C is an illustration of a sensor configuration according to one embodiment of the epidermal electronics device.

FIG. 2C illustrates an embodiment of epidermal electronics device 100 in which two sensors are arranged to measure the motion (angular and/or translational) of epidermal electronics device 100. Single-axis accelerometer 704 is shown positioned with its axis of measurement parallel to and along the Z axis of a three dimensional space. Single-axis accelerometer 704 has first angle 720 defining a zero degree angle with axis Z. Second single-axis accelerometer 706 is shown with its axis of measurement not in alignment with the axis Z. Second accelerometer 706 has an axis of measurement defined by second angle 730 from the Z axis. This angle may be greater than zero degrees. The measurement axis of second single-axis accelerometer 706 is further defined by angle 731 which defines the measurement axis relative to the X-Y plane. As is shown in the illustrated embodiment, single-axis accelerometers 704 and 706 are configured to be slightly opposed (e.g., single-axis accelerometer 704 is aligned with the Z axis and second single-axis accelerometer 706 is positioned with second angle 730 of thirty degrees and angle 731 of fifteen degrees). In some embodiments, multiple single-axis accelerometers 703 are configured to measure acceleration along the X, Y, and Z axes. In further embodiments, additional single-axis gyroscopes are configured to measure rotation about the X, Y, and Z axes in addition to acceleration along the X, Y, and Z axes. In some embodiments, one or more single-axis inclinometers are substituted for one or more accelerometers or gyroscopes. Single-axis inclinometers may also be used to provide redundant measurements. In some embodiments, the measurements provided by one or more inclinometers are used to verify the orientation of the epidermal electronics device as determined using other data. In some embodiments, single-axis gyroscopes are substituted for one or more accelerometers. Single-axis gyroscopes may also be used to provide redundant measurements. In some embodiments, the accelerometers, inclinometers, and/or gyroscopes include multi-axis accelerometers, multi-axis inclinometers, and/or multi-axis gyroscopes.

In one embodiment, single-axis accelerometer 704 is positioned on an axis. Second single single-axis accelerometer 706 is positioned along the same axis but laterally displaced from accelerometer 704. Single-axis accelerometer 704 and second single single-axis accelerometer 706 are positioned to measure acceleration along the same axis but with opposite signs. Acceleration along the axis will read as positive acceleration to one of the two accelerometers and negative acceleration to the other of the two accelerometers. Therefore, when there is acceleration without rotation, the sum of the acceleration measured by single-axis accelerometer 704 and second single single-axis accelerometer 706 will be zero or approximately zero (e.g., approximately zero accounting for measurement error, etc.). Rotation which is measured by the two accelerometers will result in a net acceleration measured by the two accelerometers. Therefore, two displaced single-axis accelerometers oppositely aligned along the same axis may detect or measure rotation, i.e., angular velocity and/or angular acceleration.

In general terms and with reference to FIGS. 1A-2C, sensors (e.g., accelerometers, inclinometers, gyroscopes, etc.) are positioned and oriented within electronics layer 107 of epidermal electronics device 100 such that angular motion and orientation of the device may be measured. Many configurations are possible and the embodiments described herein are not intended to be limiting. By using opposed or slightly opposed single-axis sensors of the types discussed, epidermal electronics device 100 may be configured to measure the orientation and/or angular motion of the device and therefore the attachment surface 103 to which the epidermal electronics device 100 is attached (e.g., a body part such as a limb, etc.). In some embodiments, a plurality of single-axis sensors are used to measure the orientation of epidermal electronics device 100. For example, six single-axis accelerometers 103 may be used to measure a total of six degrees of freedom. The six single-axis accelerometers may measure X axis acceleration, Y axis acceleration, and Z axis acceleration along with pitch, roll, and yaw angular accelerations about those axes. In some embodiments, combinations of multiple sensor types are used to achieve the same functionality. For example, three single-axis accelerometers may be configured to measure X axis acceleration, Y axis acceleration, and Z axis acceleration with an additional three single-axis gyroscopes configured to measure pitch, roll, and yaw angular velocities about those axes. Other sensors may also be used to measure the orientation, rotation, and/or position of the epidermal electronics device 100 and attachment surface 103. For example, a multi-axis accelerometer measuring X axis acceleration, Y axis acceleration, and Z axis acceleration may be used in conjunction with a multi-axis gyroscope to measure pitch, roll, and yaw angular velocities about those axes.

Figure 3A:
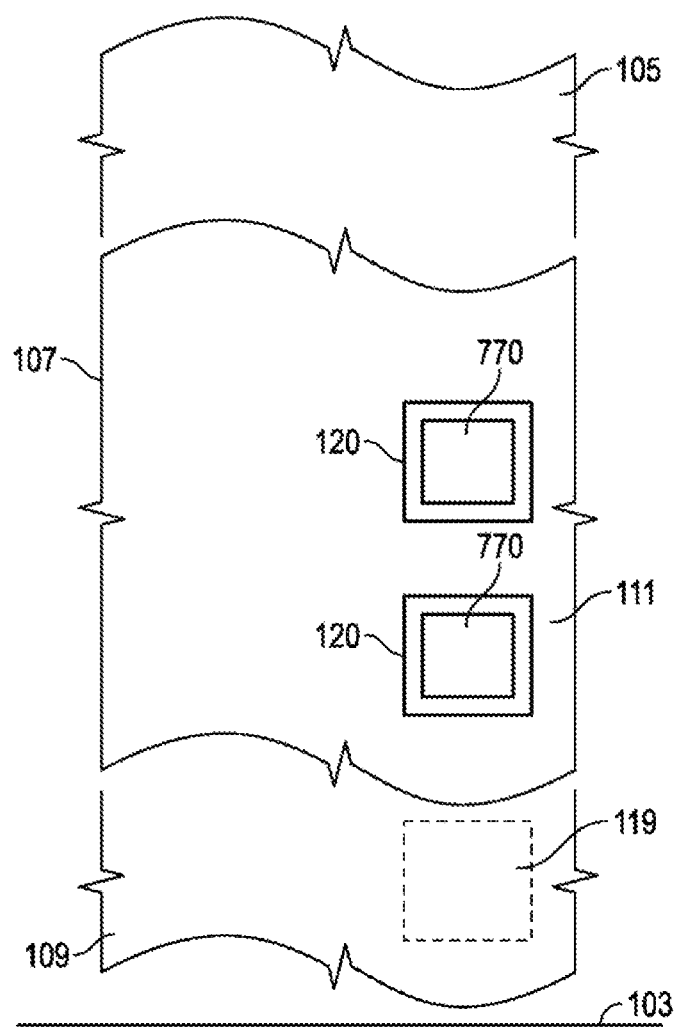
FIG. 3A is an exploded schematic view of an embodiment of the epidermal electronics device showing greater detail.

FIG. 3A illustrates an exploded schematic view of one embodiment of epidermal electronics device 100. This embodiment includes substrate layer 105, electronics layer 107 including layer of material 111, and barrier layer 109. Further included within barrier layer 109 are barrier openings 119.

Substrate layer 105 may provide physical support for electronics layer 107. Substrate layer 105 may also facilitate attachment of the epidermal electronics device 100, including electronics layer 107 and barrier layer 109, to the attachment surface 103. In some embodiments, substrate layer 105 may be discarded or dissolved after the epidermal electronics device 100 has been attached to attachment surface 103.

Electronics layer 107 is illustrated as including components on a layer of material 111. Layer 111 may be used to provide mechanical support to the components of electronics layer 107. It may also be used to facilitate manufacturing of electronics layer 107. In some embodiments, electronics layer 107 is made up only of the electronic components therein (e.g., there is no supporting layer of material). In such a case, electronics layer 107 may be manufactured on substrate layer 105 or barrier layer 109. Substrate layer 105 or barrier layer 109 provides the mechanical support necessary to make and use epidermal electronics device 100.

Substrate layer 105 provides protection to the components of the electronics layer 107. Substrate layer 105 may prevent external forces and elements from interfering with the functions of electronics layer 107. For example, substrate layer 105 may prevent moisture from reaching electronics layer 107. In some embodiments, substrate layer 105 may also prevent physical damage to the components of electronics layer 107. Substrate layer 105 may also shield electronics layer 107 from outside sources of radiation, magnetic fields, light, etc. In some embodiments, barrier layer 109 is permeable or semipermeable. For example, barrier layer 109 may be semipermeable to allow the transfer of drugs through barrier layer 109. Barrier layer 109, as depicted, may include one or more barrier openings 119. In one embodiment, barrier openings 119 correspond to a particular cell or group of cells 120. The barrier openings 119 allow for elements of electronics layer 107 to have direct contact with attachment surface 103. A sensor 770 may have direct contact with attachment surface 103 through barrier opening 119. In some embodiments, epidermal electronics device 100 may be configured with barrier openings 119 in order to better facilitate operation of one or more sensors 770. For example, allowing direct contact with attachment surface 103 may improve the accuracy of an orientation sensor such as an accelerometer. Likewise, a sensor such as a moisture sensor may have improved readings if in contact with attachment surface 103. Barrier openings 119 also facilitate the operation of interaction devices 780. Interaction devices 780 may operate more efficiently if in direct contact with attachment surface 103.

Figure 3B:
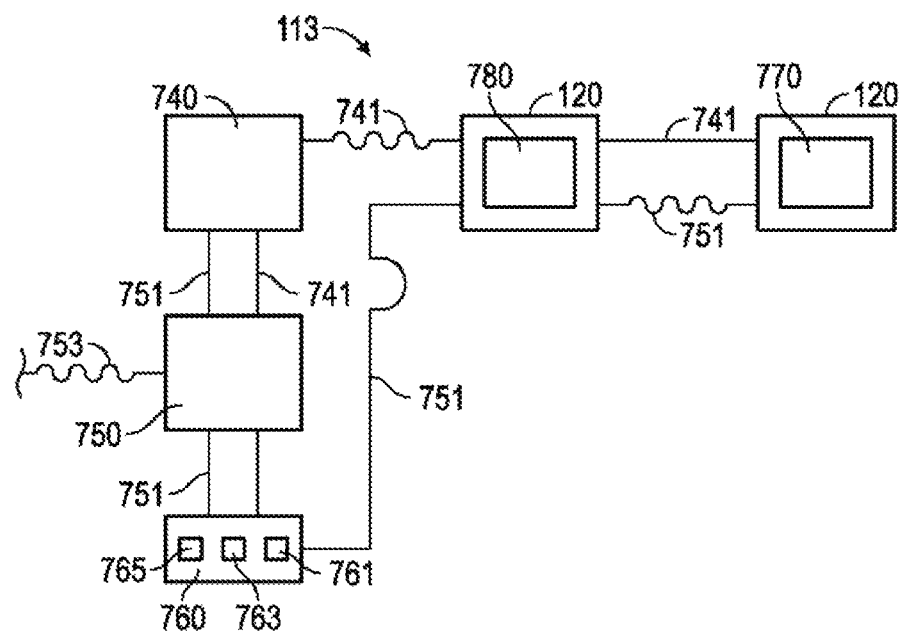
FIG. 3B is a schematic view of an embodiment of the epidermal electronics device showing greater detail of the electronics assembly.

FIG. 3B illustrates electronics assembly 113 according to one embodiment. Electronics assembly 113 includes components which are located in electronics layer 107. As depicted, electronics assembly 113 and the components therein may not be supported by an additional layer of material 111 (e.g., electronics assembly 113 may include only circuits and components without a supporting material or substrate). In some embodiments, electronics assembly 113 is produced on substrate layer 105 (not pictured in FIG. 3B). Electronics assembly 113 may include cells 120, sensors 770, interaction devices 780, power source 740 connected to other components via power connection 741, communications device 750 connected to other components via communications connection 753, control circuit 760, and input/output connection 751. In some embodiments, control circuit 760 further includes memory 761, processor 763, and multiplexer 765.

Interaction device 780 allows epidermal electronics device 100 to interact with attachment surface 103. Interaction device 780 may be configured to provide stimulation to the attachment surface in the form of applied voltage and/or drug delivery. For example, interaction device 780 may be a MEMS drug delivery system. Alternatively, interaction device 780 may be an electrode for delivering an applied voltage to the attachment surface. Interaction device 780 also allows external devices to interact with the epidermal electronics device 100. For example, a camera or motion capture system may monitor the position of the epidermal electronics device. Interaction device 780 may be a passive motion capture marker. Interaction device 780 may also be an active motion capture marker. In some embodiments, interaction device 780 is a light emitting diode (LED) controlled by control circuit 760. The LED may be illuminated intermittently to allow a motion capture system to record the orientation and/or movement of epidermal electronics device 100. This data may be used to calibrate epidermal electronics device 100. It may also be used as a constraint when estimating the orientation and movement of the epidermal electronics device from data gathered by sensors 770. For example, the orientation data from a motion capture system may be used as a boundary or limit when calculating the orientation of a body part using epidermal electronics device 100 (e.g., if a motion capture system determines that an arm has been rotated 30 degrees, a corresponding calculation made by the epidermal electronics device 100 may be limited to 30 degrees). In further embodiments, interaction device 780 includes a physiological sensor. The physiological sensor can be a wearable sensor. The physiological sensor can provide information about a user through contact with the skin of the user or proximity to the skin of the user. For example, the physiological sensor can include a heart rate sensor, a respiratory sensor, a thermal sensor, a blood pressure sensor, a hydration sensor, an oximetry sensor, an electrocardiograph, an electroencephalograph, and/or an electromyograph.

Multiple interaction devices 780 may be included in a single electronics layer 107 of epidermal electronics device 100. It is also possible for multiple interaction devices 780 to be located on more than one epidermal electronics device 100. Multiple epidermal electronics devices 100 and corresponding multiple interaction devices 780 may be coordinated and controlled using communication device 750 on each epidermal electronics device 100 as well as control circuit 760 on each epidermal electronics device 100.

Communications device 750 may be included in electronics assembly 113. Communications device 750 provides data transfer to and from the epidermal electronics device 100 through communications connection 753. Communications connection 753 may be a wire or wireless connection between communication device 750 and another source or receiver of data. For example, communications connection 753 may be a connection over a wireless network (e.g., WiFi, Zigbee, Bluetooth, etc.), a wired interface (e.g., Ethernet, USB, Firewire, etc.), or other communications connection (e.g., infrared, optical, ultrasound, etc.). In some embodiments, communications device 750 is a wireless networking device or wired networking device which establishes communication connection 753 and transmits and/or receives data/signals through communications connection 753.

Power connection 741 transfers power from power source 740 to other components in electronics layer 107. Power connection 741 provides power from power source 740 to communication device 750, control circuit 760, cells 120, and the components within cells 120 such as interaction devices 780 and sensors 770. Power connection 741 may be a wired or wireless connection. Power connection 741 may be a conductive wire (e.g., copper, aluminum, etc.). Power connection 741 may be a semiconductor. Where power connection 741 is a wired connection, power connection 741 is configured to maintain mechanical integrity when components of electronics layer 107 move relative to one another. For example, power connection 741 may be a length of wire long enough to allow movement of the components without causing deformation of power connection 741 sufficient to break the connection. Power connection 741 may also be a wireless connection for delivering power (e.g., direct induction, resonant magnetic induction, etc.).

Power source 740 provides electrical power to components within electronics layer 107. In one embodiment, power source 740 is a battery. For example, power source 740 may be a disposable battery, rechargeable battery, and/or removable battery. In some embodiments, power source 740 is configured to allow recharging of power source 740 without removing power source 740 from the electronics layer 107. For example, power source 740 may be a rechargeable battery configured to be recharged through wireless changing (e.g., inductive charging). In other embodiments, power source 740 is configured to receive direct current from a source outside the electronics layer 107. In further embodiments, power source 740 is configured to receive alternating current from a source outside the electronics layer 107. Power source 740 may include a transformer. In some embodiments, power source 740 is configured to receive power from a wireless source (e.g., such that power source 740 is a coil configured to receive power through induction). According to various alternative embodiments, power source 740 can be a capacitor which may be configured to be charged by a wired or wireless source, one or more solar cells, or a metamaterial configured to provide power via microwaves.

With continued reference to FIG. 3B, input/output connection 751 may be a wire connection between cell 120 and control circuit 760. Input/output connection 751 may be configured to allow the connection to flex and deform without suffering mechanical failure. In such a case, input/output connection 751 is configured to maintain the connection between cell 120 and control circuit 760 during deformation of the epidermal electronics device 100 due to movement of the attachment surface 103. In some embodiments, input/output connection 751 allows for deformation while maintaining mechanical integrity by including an additional length of wire which allows for connection points to separate from one another. For example, input/output connection 751 may be a wire with slack to allow two or more components to move relative to one another and not cause mechanical degradation of the input/output connection. In some embodiments, input/output connection 751 is a conductive wire (e.g., copper, aluminum, etc.). Input/output connection 751 may be a semiconductor. In some embodiments, input/output connection 751 is a wireless connection.

Input/output connection 751 allows the components within cell 120 to communicate data to control circuit 760. The component within cell 120 may output data to the control circuit through input/output connection 751. For example, sensor 770 located in cell 120 may output measurement data, in the form of a voltage, across input/output connection 751 to control circuit 760. Input/output connection 751 also allows for the control circuit to communicate with the component within cell 120. Control circuit 760 may send an input to a component within cell 120 through input/output connection 751. For example, control circuit 760 may send an input signal to interaction device 780 which causes interaction device 780 to deliver a drug or chemical to attachment surface 103. Cell 120 may also facilitate communication. Control circuit 760 may also send a calibration signal to sensor 770 or interaction device 780 using input/output connection 751. In some embodiments, power connection 741 and input/output connection 751 are integrated into a single connection. For example, an integrated connection may provide power and input/output through a modulated or otherwise alterable signal.

In some embodiments, electronics assembly 113 includes control circuit 760. Control circuit 760 may further include multiplexer 765, processor 763, and memory 761. Processor 763 may be implemented as a general-purpose processor, an application specific integrated circuit (ASIC), one or more field programmable gate arrays (FPGAs), a digital-signal-processor (DSP), a group of processing components, or other suitable electronic processing components. Memory 761 is one or more devices (e.g., RAM, ROM, Flash Memory, hard disk storage, etc.) for storing data and/or computer code for facilitating the various processes described herein. Memory 761 may be or include non-transient volatile memory or non-volatile memory. Memory 761 may include database components, object code components, script components, or any other type of information structure for supporting the various activities and information structures described herein. Memory 761 may be communicably connected to processor 763 and provide computer code or instructions to processor 763 for executing the processes described herein. Multiplexer 765 may be configured to allow multiple sensors 770 and/or interaction devices 780 to share an input/output connection 751. In some embodiments, cells 120 also facilitate multiplexing of signals from multiple components.

In some embodiments, control circuit 760 is configured to receive data from sensors 770. For example, control circuit 760 may receive acceleration data in the form of a measured voltage from an acceleration sensor. This data may be received by control circuit 760 through multiplexer 765. Control circuit 760 may store sensor data in memory 761. Control circuit 760 may output sensor data to communications device 750. In some embodiments, control circuit 760 is also configured to send control signals to sensors 770. For example, control circuit 760 may calibrate a sensor 770 by sending a control signal to the sensor. Control circuit 760 may also turn sensor 770 off or on. For example, control circuit 760 may send a control signal which causes cell 120 to disconnect sensor 770 from power connection 741. Control circuit 760 may also select which sensors to receive data from using processor 763 and memory 761. Control circuit 760 may receive control signals from communication device 750. In some embodiments, control circuit 760 also generates control signals with processor 763 and memory 761. For example, control circuit 760 may send a control signal to turn off a sensor 770 in response to abnormal data received from the sensor. Control circuit 760 may also send a control signal to turn off a sensor 770 in response to data from other sensors 770. For example, some sensors 770 may be turned off in order to conserve power source 740 if minimal acceleration is detected. When using multiple sensors, one sensor 770 may be maintained in the on position. When increased acceleration activity is detected, control circuit 760 may reactivate, or turn on, the remaining sensors 770.

In some embodiments, control circuit 760 is also configured to receive data from interaction devices 780. For example, control circuit 760 may receive drug delivery data from a drug delivery device. This data may be received by control circuit 760 through multiplexer 765. Control circuit 760 may store this data in memory 761. Control circuit 760 may output interaction device data to communications device 750. In some embodiments, Control circuit 760 is also configured to send control signals to interaction devices 780. For example, control circuit 760 may send a control signal to a drug delivery device causing the device to administer a drug to attachment surface 103. Control circuit 760 may also turn off and on interaction devices 780.

Control circuit 760 may receive signals from other components in electronics layer 107. For example, control circuit 760 may receive signals from communications device 750. Control circuit 760 may also receive signals from power source 740. For example, control circuit 760 may receive a signal from power source 740 indicating how much power is available. Control circuit 760 may use this to take further action. For example, control circuit 760 may communicate this or other information to another device using communications device 750. Control circuit 760 may also take action by controlling components of the electronics layer 107 including cells 120, interaction devices 780, and/or sensors 770. In some embodiments, the functions of control circuit 760 are carried out by the circuitry of cells 120. For example, cells 120 may include transistors and/or additional components which allow cell 120 or a network of cells 120 to perform the above described functions of control circuit 760. In other embodiments, control circuit 760 is located in an area not within electronics layer 107. In one embodiment, communications device 750 may send and receive control signals and data. For example, an external control circuit may perform the above described functions with communications device 750 relaying data between the components of the electronics layer 107 (e.g., sensors 770 and interaction devices 780) and the external control circuit.

Sensors 770 in electronics assembly 113 may include sensors configured to measure orientation data. Orientation data may include data regarding acceleration, orientation, movement, angular motion, and/or rotation of attachment surface 103. For example, sensors 770 may include one or more of single-axis accelerometers, multi-axis accelerometers, single-axis gyroscopes, multi-axis gyroscopes, single-axis inclinometers, or multi-axis inclinometers. In some embodiments, combinations of these sensors are used to measure acceleration, orientation, movement, angular motion, and/or rotation. In some embodiments, sensors 770 include sensors to measure characteristics of attachment surface 103. For example, sensors 770 may be moisture sensors, electrodes, temperature sensors (e.g., thermistors, thermocouples, etc.), light sensors, hydration sensors, etc. Interaction devices 780 may include devices configured to alter attachment surface 103 or provide data to control circuit 760. For example, interaction devices 780 may include drug delivery devices, chemical delivery devices, electrodes, motion capture sensors, LEDs, etc.

Figure 4A:
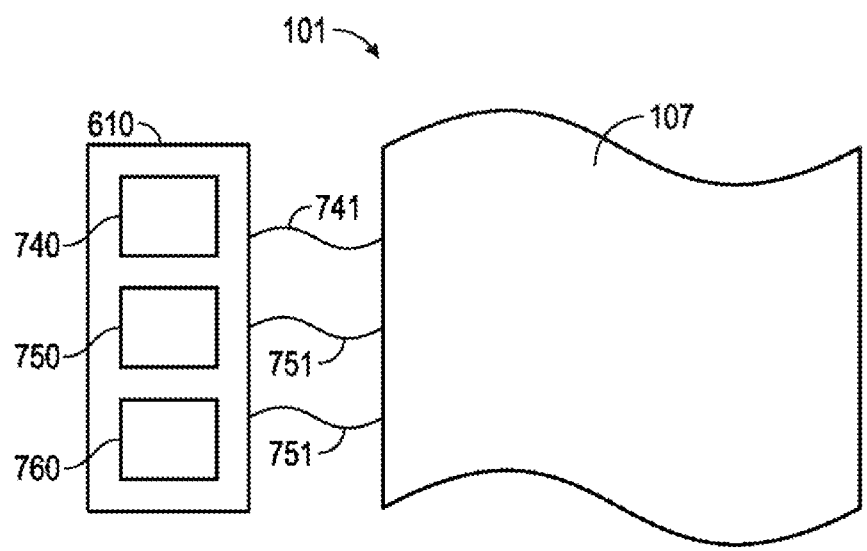
FIG. 4A is a schematic view of an additional embodiment of the epidermal electronics device.

FIG. 4A illustrates an embodiment of another epidermal electronics device shown as epidermal electronics device 101. In some embodiments, epidermal electronics device 101 houses large components in a separate housing from sensors and/or interaction devices in electronics assembly 113. These large components may be located outside of the flexible patch which includes electronics layer 107 and barrier layer 109. This is unlike epidermal electronics device 100 which includes the majority of components within electronics layer 107 (e.g., the majority of components are within the flexible patch). Epidermal electronics device 101 is shown with electronics module 610. Electronics module 610 may hold any or all of power source 740, communications device 750 and/or control circuit 760. In one embodiment, electronics module 610 is separate from electronics layer 107 shown with view 110 (e.g., electronics module 610 may house components outside of electronics assembly 113 and may provide for connection to electronics assembly 113). Electronics module 610 may be a housing containing the above mentioned components. For example, electronics module 610 may be a plastic or polymer housing with access to the components housed within. Electronics module 610 may also be a film or other protective encasement.

In some embodiments, electronics module 610 allows for power source 740, communications device 750 and/or control circuit 760 to be on a larger scale than if they were within electronics layer 107. For example, power source 740 may be a larger battery. Processing circuit 760 may be an integrated circuit or SOC. In some embodiments, electronics module 610 is connected to electronics layer 107 by power connection 741. Electronics module 610 may provide power from power source 740 to components of the electronics layer 107 (e.g., sensors, interaction devices, etc.) through power connection 741. In further embodiments, electronics module 610 is also connected to the electronics layer 107 by input/output connection 751. Electronics module 610 may be connected to electronics layer 107 and/or electronics assembly 113 by one or more input/output connections 751. This may facilitate the use of additional components (e.g., sensors, interactions devices, etc.). The use of multiple input/output connections 751 may reduce the need, partially or completely, for multiplexing.

Figure 4B:
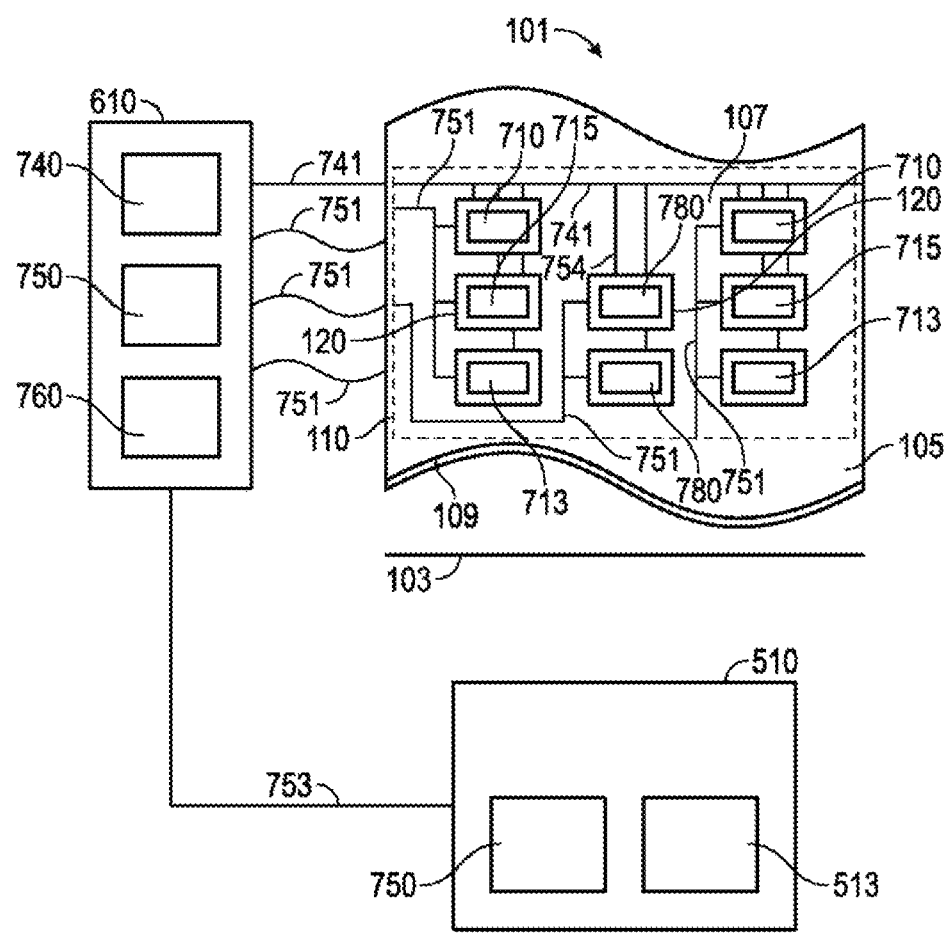
FIG. 4B is a schematic view of the electronics layer of an additional embodiment of the epidermal electronics device.

With reference to FIGS. 4A-4B, epidermal electronics devices 100 and/or 101 may measure the orientation, acceleration, movement, angular motion, rotation, angular velocity, angular acceleration, and/or position (e.g., orientation data) at one point of the attachment surface using a combination of a multi-axis accelerometer 710, multi-axis gyroscope 715, and multi-axis inclinometer 713. Using a combination of these sensors, the orientation, acceleration, movement, angular motion, rotation, angular velocity, angular acceleration, and/or position of the attachment surface may be determined with six degrees of freedom. Multiple combinations of sensors may be used to achieve measurement of six degrees of freedom.

In some embodiments, one type of sensor is used as a constraint on the measurements of another sensor. For example, the data gathered from the multi-axis inclinometer 713 may be used as a constraint on the data gathered by the multi-axis accelerometer 710 or multi-axis gyroscope 715. The angle-relative to gravity measurements of the multi-axis inclinometer may be used as a constraint on accelerometer or gyroscope data integration. In some embodiments, the sensors are integrating accelerometers. In some embodiments, measurements from inclinometers may be used directly (e.g., for angle relative to gravity). Inclinometer measurements may also be used as a check on orientation derived from the integration of data from multi-axis accelerometers 710 or from the integration of data from multi-axis gyroscopes 715. This may be used to limit error propagation. This may also include using inclinometer measurement data to verify data from other sensors and/or verify the orientation of the epidermal electronics device as determined using other data.

Epidermal electronics devices 100 and/or 101 may measure the orientation, acceleration, movement, angular motion, rotation, angular velocity, angular acceleration, and/or position at additional points of the attachment surface using additional sets of sensors. Epidermal electronics devices 100 and/or 101 may use these additional sensors (e.g., multi-axis accelerometer, multi-axis gyroscope 715, and/or multi-axis inclinometer 713) to measure orientation, acceleration, movement, angular motion, rotation, angular velocity, angular acceleration, and/or position at multiple points of the attachment surface 103 with one epidermal electronics device 100.

In some embodiments, orientation, acceleration, movement, angular motion, rotation, angular velocity, angular acceleration, and/or position are measured at multiple points using multiple epidermal electronics devices 100. Measurements from multiple epidermal electronics devices 100 and/or 101 (inter epidermal electronics device measurements) may be used as a constraint on other sensor measurements and integration. Constraints may be applied by the processing circuit 513. In some embodiments, constraints are applied by control circuit 760.

In some embodiments, multiple electronics layers 107, each with its own separate barrier layer 109 and substrate layer 105 (e.g., multiple epidermal electronics patches), connect to the same electronics module 610. This may allow for measurement and interaction at multiple points on attachment surface 103 with a single supporting power source 740, communications device 750, and control circuit 610.

With continued reference to FIG. 4B, electronics module 610 may be connected to data acquisition and processing device 510 via communications connection 753. Data acquisition and processing device 510 includes communications device 750. Communications device 750 allows data acquisition and processing device 510 to receive and send data and/or control signals to communications device 750 in electronics module 610. In some embodiments, communication device 750 in data acquisition and processing device 510 may receive and send data and/or control signals to communications device 750 in electronics layer 107 of an epidermal electronics devices 100 and/or 101.

In some embodiments, data acquisition and processing device 510 also includes processing circuit 513. Processing circuit 513 receives data from epidermal electronics devices 100 and/or 101. Processing circuit 513 analyzes the data. For example, processing circuit 513 may use algorithms to calculate or estimate the orientation, acceleration, movement, rotation, angular velocity, and/or position of the epidermal electronics devices 100 and/or 101. These algorithms may include a Kalman filter, dynamic filter, a customized algorithm, etc. Processing circuit 513 may calculate or estimate the orientation, acceleration, movement, angular motion, angular acceleration, rotation, angular velocity, and/or position of one or more locations on an epidermal electronics device 100 and/or 101 or multiple epidermal electronic devices 100 and/or 101.

In some embodiments, processing circuit 513 also sends control signals to epidermal electronics device 100. For example, processing circuit 513 of data acquisition and processing device 510 may send a control signal to epidermal electronics device 100, using communication devices 750, to calibrate sensor 770. To facilitate the above functions, processing circuit 513 and/or data acquisition and processing device 510 may include one or more of processors and memory.

Data acquisition and processing device 510 may output data, control signals, and/or estimations or calculations regarding orientation, acceleration, movement, angular motion, rotation, angular velocity, angular acceleration, and/or position to additional computing devices. Data acquisition and processing device 510 may also output to one or more epidermal electronics devices 100 and/or 101. This may include outputting data gathered by one epidermal electronics device 100 or 101 to a second epidermal electronics device 100 or 101. In some embodiments, data acquisition and processing device 510 includes a user interface. In other embodiments, data acquisition and processing device 510 is controlled with an additional computer. In some embodiments, data acquisition and processing device 510 may also output data to another computer. In some embodiments, an epidermal electronics device 100 with power source 740, communications device 750, and control circuit 760 integrated in electronics layer 107 is connected to data acquisition and processing device 510.

Figure 5:
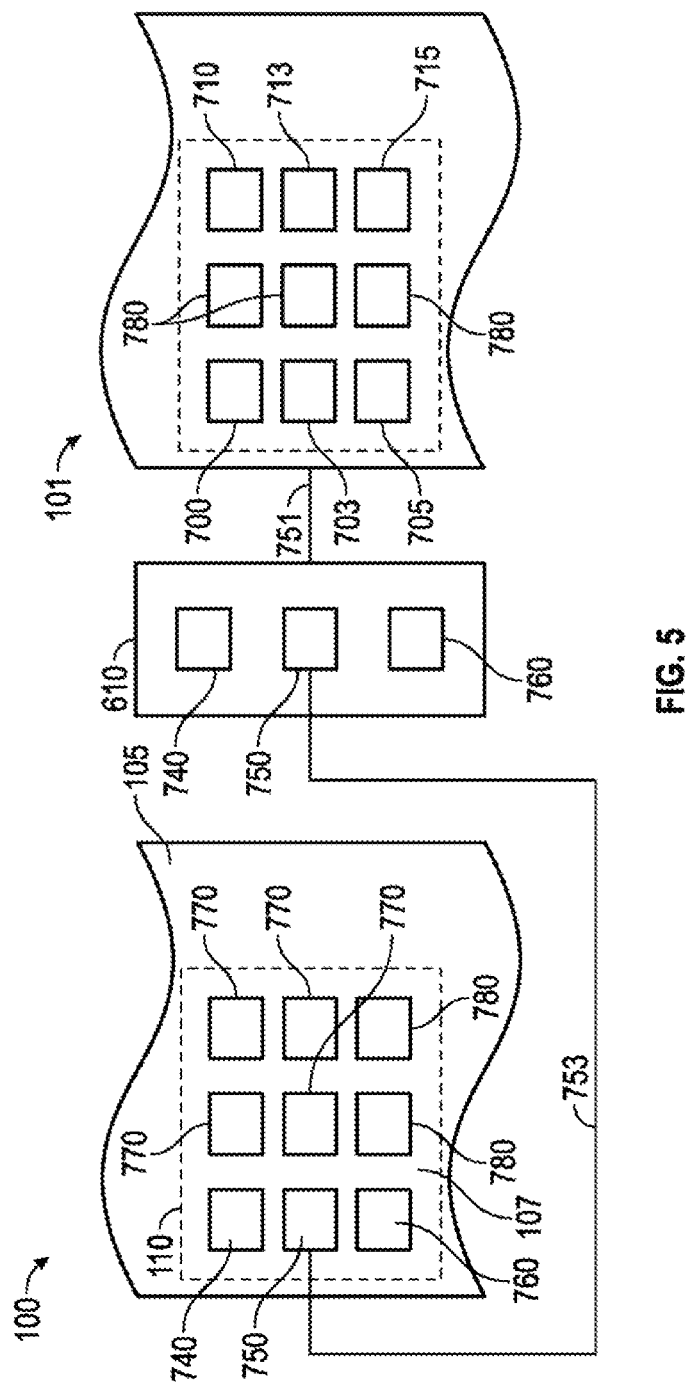
FIG. 5 is a schematic view of two embodiments of the epidermal electronics device in communication with each other.

FIG. 5 illustrates an embodiment of epidermal electronics devices 100 and 101 in communication with one another. Two or more epidermal electronics devices 100 or 101 may communicate with one another through communications connection 753 and communication devices 750. Communications connection 753 may be a wireless connection or a wired one. Multiple epidermal electronics devices 100 may also communicate with data acquisition and processing device 510. Using two or more epidermal electronics devices 100 or 101 allows for multiple points to be measured simultaneously. For example, the orientation, acceleration, movement, rotation, angular velocity, angular acceleration, and/or position of one point may be measured relative to that of another through the use of two or more epidermal electronics devices 100.

Figure 6:
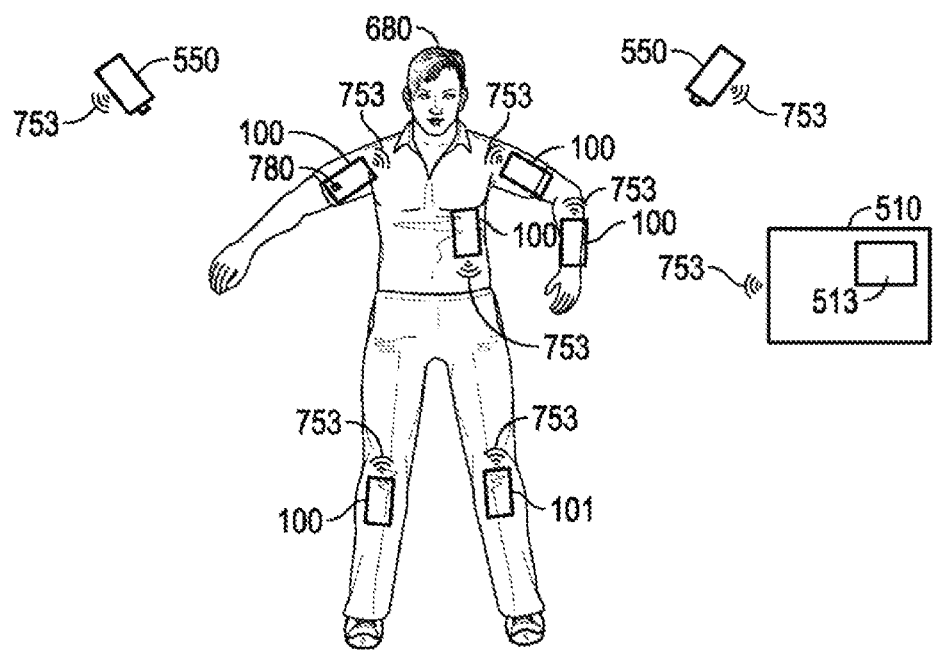
FIG. 6 is a schematic view of an embodiment the epidermal electronics device as used to measure orientation relative to several body parts.

FIG. 6 illustrates one embodiment of multiple epidermal electronics devices 100 used with user 680. In one embodiment, multiple epidermal electronics devices 100 are attached to user 680. Epidermal electronics devices 100 may communicate using wireless communications connection 753. Data may be communicated to data acquisition and processing device 510 which may include processing circuit 513. External sensing devices 550 may also be used to gather information about user 680 and/or epidermal electronics devices 100. External sensing devices 550 may also communicate data with wireless communication connection 753.

In one embodiment, epidermal electronics devices 100 are placed on various body parts of user 680. For example, epidermal electronics devices may be placed on fingers, hands, forearms, upper arms, feet, legs, the head, etc. In some embodiments, the attachment surface 103 of user 680 is his or her skin. Each epidermal electronics device may measure orientation with one of or a combination of single or multi-axis accelerometers, single or multi-axis inclinometers, or single or multi-axis gyroscopes. Epidermal electronics devices 100 may communicate with one another and/or with data acquisition and processing device 510 using communications connection 753 and communications devices 750. In this embodiment, communications connection 753 is illustrated as a wireless connection. In some embodiments, epidermal electronics devices 100 may form a network (e.g., ad hoc network). The network of epidermal electronics devices 100 may communicate data and control signals to other networks of epidermal electronics devices 100. Multiple networks of epidermal electronics devices 100 may share information. This may allow data to be collected from multiple networks (e.g., one network per user, with multiple users) by a single data acquisition and processing device 510.

FIG. 6 further illustrates that two or more epidermal electronics devices 100 may be used to measure attachment surface parameters (e.g., orientation, acceleration, movement, angular motion, rotation, angular velocity, angular acceleration, and/or position) relative to one another. As is illustrated, the attachment surface parameters of a forearm may be measured relative to the attachment surface parameters of an upper arm. This allows epidermal electronics devices 100 and data acquisition and processing device 510 to determine the orientation or movement of the forearm relative to the upper arm. The relative orientation, acceleration, movement, angular motion, rotation, angular velocity, angular acceleration, and/or position of one body part to another may be measured in this way. For further example, the orientation of a finger may be determined relative to a hand. Epidermal electronics devices 100 may also be used to measure a change in attachment surface parameters. Such changes may be used to determine motion of a user, such as gait, gestures, athletic motions (e.g., golf swings, pitching motions, etc.), or the like. This measurement may be made absolutely by a single epidermal electronics device 100 or relative to an additional one or more epidermal electronics device 100. For example, as a user's leg moves, the change in orientation and angular velocity may be measured. This measurement may be made absolutely by epidermal electronics device 100. The measurement may also be made relative to the moving torso of user 680. In that case, measurements are collected by epidermal electronics device 100 on the torso and epidermal electronics device 100 on the leg. The relative orientation and angular velocity may be calculated by data acquisition and processing device 510. In some embodiments, a single epidermal electronics device 100 may be used to measure attachment surface parameters at multiple locations. This may include multiple locations across multiple body parts. For example, a single epidermal electronics device 100 may measure the orientation of the torso and a leg of user 680.

Data acquisition and processing device 510 may use a variety of techniques to determine or estimate the orientation, acceleration, movement, angular motion, rotation, angular velocity, angular acceleration, and/or position of user 680. Data acquisition and processing device 510 may also use the same or other techniques to determine the posture and/or gestures of user 680. These techniques may include applying algorithms, Kalman filters, and/or other dynamic filters to measurements and/or applying constraints provided by one or more epidermal electronics devices 100. For example, a Kalman filter may be used to estimate the orientation of epidermal electronics device 100 attached to a body part of a user. The orientation can be described by various types of state vectors, such as Euler angles, quaternions, etc. Because some of the sensors used by epidermal electronics device 100 measure angular motion (e.g., angular velocity via gyroscopes, angular acceleration via accelerometers) rather than directly measuring orientation (e.g., via inclinometers, field sensors, etc.) physics-based dynamic filters (e.g., Kalman filters) can be used to estimate the orientation. Such filters may incorporate additional state variables (such as angular velocity and/or angular acceleration), which are linked via a state propagation model (e.g., continuous propagation via differential equations, discrete propagation via state transition matrices). The dynamic filter incorporates measurements related to the state variables (e.g., opposed accelerometer measurements for angular acceleration, gyroscope measurements for angular velocity, inclinometer or field measurements for angular orientation, etc.) each of which may depend on a single state variable or multiple ones (e.g., angular motion measurements often also depend on the direction of the sensor, and hence on the orientation). The dynamic filter can include estimates of the noise in such measurements, and hence in the uncertainty in its estimate of each state variable; these uncertainty estimates can be tracked throughout time by the filter. Dynamic filters can readily be formulated to handle different state vector representations (e.g., angles vs quaternions), different measurement types (combinations of direct angular measurements and/or angular velocity and/or angular acceleration), and different sensors (e.g., magnetometers vs inclinometers, rotational vs ring-laser vs vibratory gyroscopes). A comparison of various dynamic filters for use in body sensor networks is presented in "Analysis of Filtering Methods for 3D Acceleration Signals in Body Sensor Network", Wei-zhong Wang, Bang-yu Huang, Lei Wang, Bulletin of Advanced Technology Sensors, Vol 5, No 7, 2011. Presentations of Kalman filters used for 3D orientation estimation include: "Design, Implementation, and Experimental Results of a Quaternion-Based Kalman Filter for Human Body Motion Tracking", Xiaoping Yun, Eric Bachmann, IEEE Transactions on Robotics, Vol 22, No 6, 2006; "Kalman-Filter-Based Orientation Determination Using Inertial/Magnetic Sensors: Observability Analysis and Performance Evaluation", Angelo Sabatini, Sensors, Sep. 27, 2011; "Using an Extended Kalman Filter for Rigid Body Pose Estimation", Kjartan Halvorsen, et al, Journal of Biomechanical Engineering, Vol 127, p 475 (2005); and "An Extended Kalman Filter for Quaternion-Based Orientation Estimation Using MARG Sensors", Joao Marins, et al, 2001 IEEE/RSJ International Conference on Intelligent Robots and Systems, Maui Oct. 29-Nov. 3, 2001. In some embodiments, constraints are supplied by other sources such as models of human movement, external sensing devices, etc. In some embodiments, constraints may define ranges in which the measurements of epidermal electronics device 100 may be considered valid. Data acquisition and processing device 510 may combine various measurements and/or constraints using a Kalman or other dynamic filter. This may result in a better estimate of unknown variables than one based on one measurement or data point. Additionally, signal noise and inaccuracies may be reduced.

Multiple epidermal electronics devices 100 may also be used to measure the state of user 680. Epidermal electronics devices may be used to measure the posture of user 680. By measuring orientation, acceleration, movement, angular motion, rotation, angular velocity, angular acceleration, and/or position at one or more locations, the user's posture may be determined. For example, it can be determined whether a user 680 is sitting, standing, or lying down using inclinometers and accelerometers measuring various body parts. If a person is sitting, inclinometers on the torso and on a leg will give different readings of the angle relative to gravity. Corresponding accelerometer or gyroscope readings indicating little or no acceleration could indicate that a user 680 is sitting. Alternative configurations and sensors may be used to detect a variety of postures. In some embodiments, the posture measured includes the positioning of one or more body parts during movement or a particular type of movement. For example, epidermal electronics devices 100 may measure the posture of a user 680 while running to ensure proper form or to be used to improve form. For example, epidermal electronics devices 100 may measure the posture of a user 680 while swinging a golf club to ensure proper form or to be used to improve form. In some embodiments, a single epidermal electronics device 100 may be used to measure attachment surface parameters at multiple locations.

Multiple epidermal electronics devices 100 may be used to measure gestures made by user 680. The orientation, acceleration, movement, angular motion, rotation, angular velocity, angular acceleration, and/or position of specific body parts along with the change in the same parameters may be measured. For example, epidermal electronics devices 100 placed on the fingers, hands, and arms may be used to detect gestures made using those body parts. For example, measuring the orientation, acceleration, movement, angular motion, rotation, angular velocity, angular acceleration, and/or position of those body parts along with the change in the same parameters may allow for sign language to be interpreted. In some embodiments, gestures are defined as any particular movement or movements of one or more body parts. Epidermal electronics device 100 may measure movements, and data acquisition and processing device 510 may compare the movements to a library of gestures. The library of gestures may contain the movements comprising gestures. Using the comparison, data acquisition and processing device 510 may estimate or determine if a gesture has been made.

In determining the posture and/or gestures of user 680, a human model may be used in conjunction with one or more epidermal electronics devices 100 and data acquisition and processing device 510. A human model may be a computer model of human movement and provide a way of checking measured movements against a model of all possible movements. A human model may include a human connectivity model, a musculoskeletal model, or other model of movement. The human connectivity model may model a human as an interconnected set of rigid bodies with defined shapes, connected via joints with defined angular constraints. Presentations of such models include: "Motion Models for People Tracking", David Fleet, Visual Analysis of Humans, Chapter 10, Springer-Verlag (2011); and "A 3-D Biomechanical Skeleton Model for Posture and Movement Analysis", Moreno D'Amico, et al, Research into Spinal Deformities 5, IOS Press (2006). This system of defined rigid bodies, interconnectivities, and joints can be used to model postures and postural motions based upon orientation sensing epidermal electronics devices on one or more body parts. The model may be generic or may be personalized for an individual user. In some embodiments, a generic or personalized model is adjusted using measurements provided by epidermal electronics device 100. The human model may be used by the data acquisition and processing device to assist in determining or estimating the posture and/or gestures of user 680. For example, a human connectivity model may be used as a constraint on sensor measurements and integration when determining or estimating the orientation, acceleration, movement, angular motion, rotation, angular velocity, angular acceleration, and/or position of a point measured by epidermal electronics device 100. In some embodiments, further constraints include measurements from additional sensors such as inclinometers. The measurements from one or more inclinometers or magnetometers may be used as a check on orientation estimated from an accelerometer. This technique may be used to limit error propagation. In some embodiments, further constraints may also include inter epidermal electronics device measurements.

With continued reference to FIG. 6, one or more external sensing devices 550 may be used in conjunction with epidermal electronics device 100. In some embodiments, external sensing device 550 is a device external to epidermal electronics device 100 used to measure orientation, acceleration, movement, angular motion, rotation, angular velocity, angular acceleration, and/or position. External sensing device 550 may be a camera or motion capture image sensor. External sensing devices 550 may be used to intermittently make measurements to determine posture. For example, images from external cameras may be used to measure the orientation, acceleration, movement, angular motion, rotation, angular velocity, angular acceleration, and/or position of a user 680. In some embodiments, measurements from motion capture image sensors of active or passive interaction devices 780 are used to determine the orientation, acceleration, movement, angular motion, rotation, angular velocity, angular acceleration, and/or position of a user 680. Measurements from one or more external sensing devices 550 may be used to reset epidermal electronics device 100 based determinations. For example, measurements taken from an external sensing device 550 may be used to calibrate the sensors of one or more epidermal electronic devices 100. In some embodiments, the measurements from external sensing devices 550 may be used to update or individualize a human model for a user 680. The human model may also serve as a calibration point for the sensors of one or more epidermal electronics devices 100. Interaction devices 780 may also be calibrated in the same fashion. In some embodiments, external sensing device 550 is connected to data acquisition and processing device 510 via communication connection 753. External sensing device 550 may include communications device 750 to facilitate communication via communication connection 753. In some embodiments, external sensing device 550 may be connected to control circuit 760 via communications connection 753 and communications device 750.

In one embodiment, an epidermal electronics device 100 determines its position and/or movement relative to another location using an antenna and a field source at the other location. Sensors 770 may be or include one or more antennas. For example, the antenna or antennas may be one or more of a dipole antenna, loop antenna, plate antenna, magnetometer, vector magnetometer, and/or other types of antennas. Epidermal electronics device 100 may use one or more antennas to measure a field source. Based on the measurement of one or more field source, epidermal electronics device 100 may estimate the location, orientation, angular motion, rotation, and/or other movement of epidermal electronics device 100 relative to the field source.

The field source may be a source of any measureable field. For example, the field source may be a source of a magnetic field, electromagnetic radiation (e.g., microwaves, radio waves, etc.), and/or other source of a measureable field. The field source may be a microwave generator and/or antenna, radio transmitter and/or antenna, or other combination of hardware configured to generate a measureable field. In some embodiments, a natural field source can be used, for instance epidermal electronics device may use a magnetometer to measure the Earth's magnetic field, and hence determine one or more angular components of its orientation. Epidermal electronics device 100 may include one or more antennas for measuring the type of field generating by the field source. Epidermal electronics device 100 may include additional hardware for the reception and/or measurement of one or more field sources. For example, epidermal electronics device 100 may include a receiver, signal processing hardware, and/or other hardware.

In one embodiment, the field source is emitted by a second epidermal electronics device 100. This may allow the first epidermal electronics device 100 to determine its location, orientation, angular motion, rotation, and/or other movement relative to the second epidermal electronics device 100 which emits the field source. Orientation information may be sent from the other location to epidermal electronics device 100 containing information about the field source, e.g., type, spatial field pattern, frequency, orientation of the source, etc. The field source may be or be included in interaction device 780. In other embodiments, the field source may be fixed. For example, the field source may be a fixed emitter which generates a field encompassing one or more separate epidermal electronics devices 100. As the field source is fixed, one or more epidermal electronics devices 100 may measure individual absolute location, orientation, angular motion, rotation, and/or other movement relative to the fixed field source. The fixed field source may be included in data acquisition and processing device 510 or another fixed device. In some embodiments, one or more epidermal electronics devices 100 may determine their location, orientation, rotation, angular motion, and/or other movement relative to other epidermal electronics devices 100. In some embodiments, the epidermal electronics device may estimate its absolute location, orientation, rotation, angular motion, and/or other movement by combining the relative information with corresponding absolute information for the other epidermal electronics devices.

In one embodiment, an epidermal electronics device 100 determines its position and/or orientation relative to another location (e.g., a second epidermal electronics device) using a range sensor and a range-determination source at the other location. Range sensors may include one or more receivers for detecting a range signal generated by the range-determination source. For example, the range-determination source may generate range signals comprising pulsed ultrasound waves or pulsed electromagnetic waves. The range sensor (an ultrasound or an electromagnetic detector respectively) can detect the incident waves and, based on time-of-arrival, determine the range between the range-determination source and the range sensor. A single range sensor can be used to detect the range itself. However, in some embodiments, epidermal electronics device 100 comprises multiple range sensors, and uses the differential ranges of each from the range-determination source, to determine the orientation of epidermal electronics device relative to the range determination source. Orientation information may be sent from the other location to epidermal electronics device 100 containing information about the range-determination source, e.g., pulse timing, wave frequency, emission pattern, orientation of the source, etc. For example, two range sensors can be used to determine one angular component of the orientation, while three range sensors can be used to determine two angular components of the orientation. In one embodiment, the roles of the range sensor and the range-determination sources can be reversed; here epidermal electronics device 100 can comprise multiple (e.g., 2 or 3) range-determination sources, and another location (e.g., a second epidermal electronics device) can comprise a range sensor. Differential range measurements by the range sensor can be used to determine the orientation of epidermal electronics device 100. In some embodiments, epidermal electronics device 100 comprises both one or more range-determination sources and one or more range sensors, using reflectors (e.g., diffuse, specular, or retro) at another location to return range signals from the range-determination source to the range sensors, allowing determination of the range and/or orientation between epidermal electronics device 100 and the other location.

In further embodiments, a plurality of fields may be used to measure location, orientation, rotation, angular motion, and/or other movement relative to multiple field sources (fixed and/or moving). For example, field sources may have different timings or frequencies in order to allow epidermal electronics devices 100 to distinguish between a plurality of field sources. This may allow for additional techniques for estimating the location, rotation, and/or other movement of one or more epidermal electronics devices. For example, epidermal electronics device 100 may triangulate its location using a plurality of field sources.

In other above described embodiments, the estimation of absolute and/or relative position, orientation, rotation, angular motion, and/or other movement may be calculated by one or more epidermal electronics device 100. For example, calculations may be performed using one or more control circuits on one or more epidermal electronics devices 100. Epidermal electronics devices 100 may communicate information for use in these calculations using one or more of the techniques described herein. In other embodiments, calculations are performed remote from the epidermal electronics devices 100. For example, one or more epidermal electronics devices 100 may communicate information (e.g., field measurements) to data acquisition and processing device 510 which may perform the calculations described herein.

Still referring to FIG. 6, measurements and/or estimates of location, position, orientation, rotation, and/or other movement may be used in performing a variety of actions and/or further calculations. Orientation, motion, and/or location may be used as a parameter to control one or more interaction devices 780. For example, orientation, motion, or location may be used to control a drug delivery system. If user 680 is lying down (e.g., as determined by epidermal electronics device 100 and/or data acquisition and processing device 510), a drug delivery system may be instructed not to deliver pain medication. Conversely, if a user 680 is moving, the drug delivery system may be instructed by data acquisition and processing device 510 and/or control circuit 760 to administer pain medication.

By measuring the orientation, acceleration, movement, angular motion, rotation, angular velocity, angular acceleration, and/or position and/or the change in the foregoing after an interaction device has been triggered, the effect of the interaction may be measured. This may also allow the interaction device 780 to be calibrated. For example, if a measured parameter (e.g., posture of user 680 during movement) does not show improvement, a larger dose of a drug may be used next time the interaction device 780 is activated.

Additionally, orientation, motion, and/or location may be used to control sensors 770. For example, if a user is in a lying down position, sensors 770 and/or interaction devices 780 may be turned off to conserve power. In some embodiments, any of the parameters described herein (e.g., orientation, posture, acceleration, etc.) may be used as the basis of an alert. Epidermal electronics device 100 may provide an alert when a certain parameter or parameters exceeds a threshold. For example, if rapid acceleration in an event such as a car crash is detected, LEDs on the epidermal electronics device may be illuminated, or illuminated in a particular color corresponding to severity, to alert a viewer as to possible injury. This type of configuration may be used in other settings as well (e.g., physical therapy). In some embodiments, the alert is provided by data acquisition and processing device 510. Data acquisition and processing device 510 may provide the alert using a display. Data acquisition and processing device 510 may provide the alert to another device or computer (e.g., provide an alert to a mobile computing device or phone).

Figure 7:
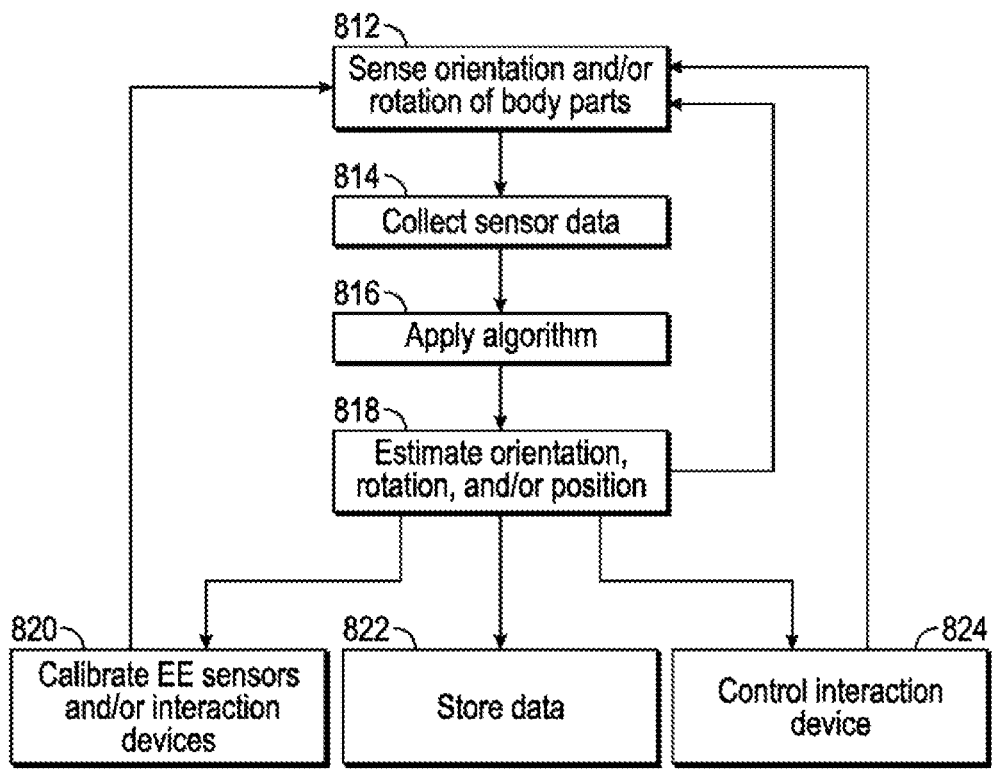
FIG. 7 is a flow chart detailing operation of one embodiment of the epidermal electronics device.

Referring now to FIG. 7, method 810 of using one or more epidermal electronics devices to measure orientation is shown according to one embodiment. Data regarding the orientation and/or angular motion of the surface to which the epidermal electronics device is attached is provided (812). This may be accomplished with any combination of sensors previously described. The sensor data is then collected (814). For example, a control circuit may collect/acquire the data. The control circuit may collect/acquire the data using, in part, a multiplexer. In some embodiments, cells assist in multiplexing. In some embodiments, the sensor data is then communicated to a data acquisition and processing device. This may be done using a combination of the control circuit and the communications device. An algorithm is applied to the sensor data (816). In some embodiments, the data acquisition and processing device applies the algorithm. In other embodiments, the control circuit applies the algorithm. One or more algorithms may be used, and the algorithms may perform a variety of functions. For example, algorithms may be used to reduce signal noise, eliminate extraneous data points, generate constraints for calculating the orientation and/or position of the attachment surface, etc. The algorithms used may include a Kalman filter, dynamic filter, or other custom filter. The orientation, motion, rotation, and/or position of the attachment surface and/or epidermal electronics device is estimated or calculated (818). In some embodiments, the data acquisition and processing device uses the sensor data and/or constraints to estimate or calculate orientation, motion, rotation, and/or position of the attachment surface and/or epidermal electronics device. In other embodiments the control circuit uses the sensor data and/or constraints to estimate or calculate orientation, motion, rotation, and/or position of the attachment surface and/or epidermal electronics device. In further embodiments, one or more algorithms are also used to perform calculations. Posture may be estimated in addition to or instead of orientation, rotation, and/or position of the attachment surface and/or epidermal electronics device. In some embodiments, the location, orientation, motion, and/or rotation of a body part may be referenced to a position in/on the body part which differs from that of the attachment surface and hence epidermal electronics device 100 (for instance, the reference site of a forearm may be at the midpoint of the radius bone while the attachment surface is located on the outer skin surface near the wrist; in such cases, the locations, orientations, motions, and rotations at the two locations may differ by straightforwardly applied offsets. In performing these calculations (e.g., to determine orientation or posture), the data acquisition and processing device may use constraints or checks generated from other sources. For example, constraints may be supplied by the algorithms, additional sensors such as inclinometers, and/or external sensing devices such as motion capture image sensors. Following the estimation or calculation of the orientation, rotation, motion, and/or position of the attachments surface, the epidermal electronics device may begin the cycle again by using sensors to produce data regarding the orientation and/or rotation of the surface to which the epidermal electronics device is attached. In some embodiments, steps (812)-(818) are performed simultaneously as in data pipelining. For example, as a first set of data is being used to calculate orientation, a second set may be filtered using an algorithm, a third set may be collected by the control circuit, and a fourth set may be generated by the sensors.

Simultaneously with the next cycle of steps, additional actions may be taken. In some embodiments the additional actions are taken before the next cycle of steps begins. After the estimation or calculation of the orientation, rotation, and/or position of the attachments surface, the sensors and/or interaction devices may be calibrated (820). The data acquisition and processing device may determine that a sensor and/or interaction device needs to be calibrated. Using data from other sensors onboard the epidermal electronics device, data from external sensing devices, models, and/or calculated constraints, the data acquisition and processing device, in conjunction with the control circuit, may calibrate a sensor or interaction device. In some embodiments, the calibration is done solely by the control circuit. The data acquisition and processing device may be able to override a predetermined calibration algorithm run by the processing circuit. In addition to calibrating sensors and/or interaction devices and/or controlling an interaction device, or in isolation, various types of data may be stored (822). In some embodiments, data is stored by the data acquisition and processing device. In other embodiments, data is stored by the control circuit. The data may be stored locally within the data acquisition and processing device or may be transferred to an additional computer, display device, mobile device, etc. In some embodiments, the results and/or only a portion of the data is stored. In some embodiments, the data is temporarily stored such that a device may display the data and/or a graphical representation of the data. In addition to calibrating sensors and/or interaction devices and/or storing data, or in isolation, one or more interaction devices may be controlled (824). The data acquisition and processing device, in conjunction with the control circuit, may activate one or more interaction devices. For example, upon determining a particular orientation of a user, the data acquisition device and control circuit may activate an interaction device to deliver a drug. In some embodiments, interaction devices are controlled by the control circuit without input from a data acquisition and processing device.

Figure 8:
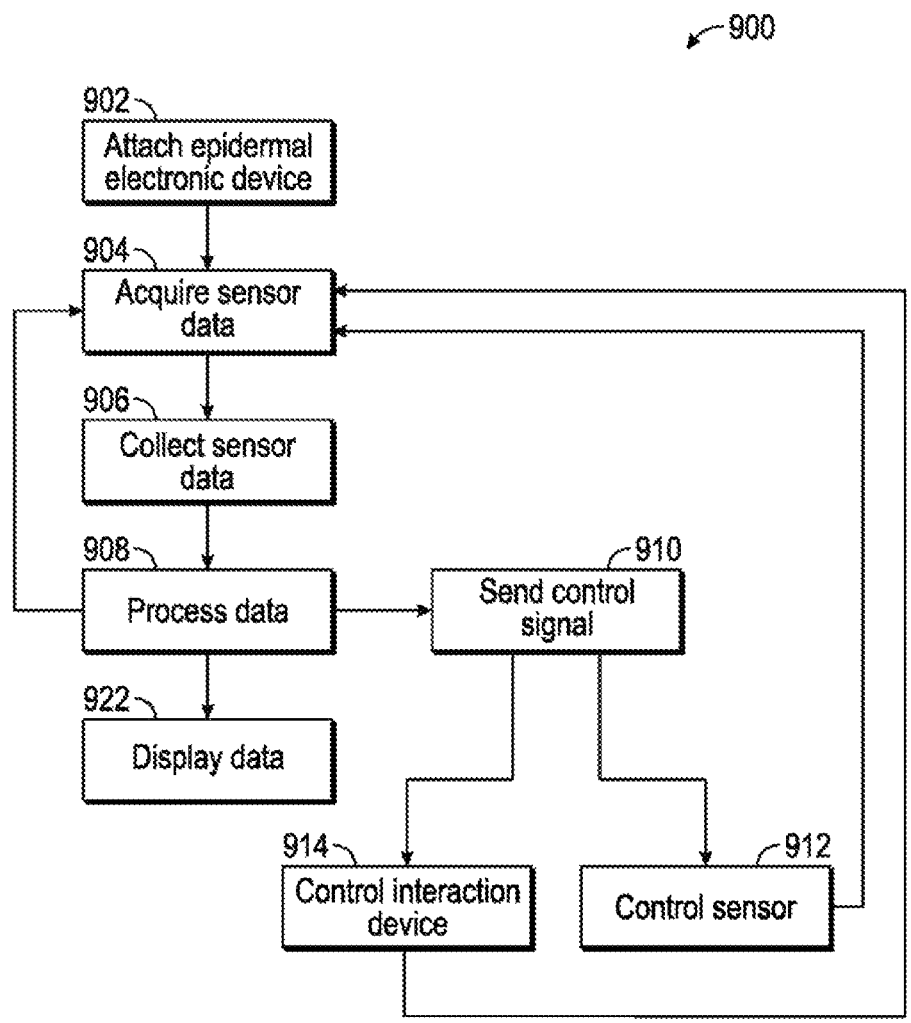
FIG. 8 is a flow chart with additional detail showing the operation on an embodiment of the epidermal electronics device.

Referring now to FIG. 8, method 900 of operation of an epidermal electronics device is shown according to one embodiment. The epidermal electronics device is attached (902). The epidermal electronics device is attached to attachment surface 103 which may include skin, bone, muscle tissue, the heart, the lungs, etc. In some embodiments, attachment surface 103 is a bandage attached or to be attached to the skin or other organ. Sensor data is acquired (904). Acquiring sensor data may include measuring one or more parameters of attachment surface 103. In some embodiments, sensors 770 in epidermal electronics device 100 measure one or more parameters of attachment surface 103. For example, sensors 770 may measure the orientation of attachment surface 103 as approximated by the orientation of electronics layer 107 in epidermal electronics device 100. Sensors 770 may also measure the rate of change in the orientation, acceleration, movement, angular motion, rotation, angular velocity, angular acceleration, and/or position of attachment surface 103. In some embodiments, the rate of change of these parameters is calculated by either control circuit 760 or data acquisition and processing device 510. The sensor data is collected (906). For example, the sensor data is collected by control circuitry. This may be accomplished using multiplexer 765 within control circuit 760. The data is processed (908). For example, control circuit 760 may use processor 763 and memory 761 to calculate the orientation of epidermal electronics device 100. The data may be processed by a variety of techniques to estimate or calculate orientation, acceleration, movement, angular motion, rotation, angular velocity, angular acceleration, and/or position of epidermal electronics device 100. For example, control circuit 760 may use a Kalman filter, dynamic filter, or other algorithm to calculate or estimate the orientation of epidermal electronics device 100. Control circuit 760 may also use constraints in making calculations such as data from other sensors 770 in epidermal electronics device 100, data from another epidermal electronics device 100, data from external sensing devices 550, and/or models. Control circuit 760 may also monitor sensors 770 for irregular measurements.

After acquiring and processing the data, the data is displayed (922). In some embodiments, control circuit 760 sends the data to data acquisition and processing device 510 to be displayed. In other embodiments, data acquisition and processing device 510 displays the data. The data displayed may be one of or a combination of the raw sensor data, constraints, models, processed data, estimated orientation, acceleration, movement, angular motion, rotation, angular velocity, angular acceleration, and/or position of the attachment surface, graphical representations of position, orientation, gait, and/or posture, etc. In some embodiments, the data is displayed on another computer or device to which data acquisition and processing device 510 sends the relevant information. Method 900 may begin again by measuring one or more parameters with sensors 770 of epidermal electronics device 100. In some embodiments, several iterations take place prior to the display of data. In some embodiments, only one iteration of the steps occurs.

In some embodiments, a control signal is sent (910) following the processing of data by control circuit 760. The control signal may be sent to sensor 770 and/or interaction device 780. In the case that the control signal is sent to sensor 770, the sensor 770 is controlled (912). This may include calibrating sensor 770. This may also include turning sensor 770 on or off. In the case that the control signal is sent to interaction device 780, interaction device 780 is controlled (914). This may include activating interaction device 780, for example, delivering a drug with a drug delivery device. Controlling interaction device 780 may also include turning interaction device 780 on or off. After controlling sensor 770 or controlling interaction device 780, the method may begin again by measuring one or more parameters with sensors 770 of epidermal electronics device 100.

In some embodiments, control circuit 760 outputs data using communications device 750 and communications connection 753 after the data has been processed. In other embodiments, the data which is output may not have been previously processed (e.g., control circuit 760 may output measurement data from sensors 770 without estimating or calculating orientation). The data may be output to data acquisition and processing device 510. In some embodiments, the data is output to other devices. For example, data may be output to other epidermal electronics devices 100 or to a computer other than data acquisition and processing device 510. The output data may be acquired and processed. In some embodiments, data is acquired and processed by data acquisition and processing device 510. Data acquisition and processing device 510 may acquire the data through communications device 750 and communications connection 753 with epidermal electronics device 100. The data may be processed by a variety of techniques to estimate or calculate orientation, acceleration, movement, angular motion, rotation, angular velocity, angular acceleration, and/or position of epidermal electronics device 100. For example, data acquisition and processing device 510 may use a Kalman filter, dynamic filter, or other algorithm to calculate or estimate the orientation of epidermal electronics device 100. Data acquisition and processing device 510 may also use constraints in making calculations such as data from other sensors 770 in epidermal electronics device 100, data from another epidermal electronics device 100, data from external sensing devices 550, and/or models. In further embodiments, a control signal may be sent following the acquisition of the data from sensors 770 and processing of the data by data acquisition and processing device 510. Data acquisition and processing device 510 may send the control signal following the acquisition and processing of the data. The control signal may be sent to control circuit 760 using communication device 750 and communication connection 753. In some embodiments, control circuit 760 uses the data or information transferred to send control signals as instructed by data acquisition and processing device 510. Control circuit 760 may also send a control signal to one or more interaction devices 780 and/or one of more sensors 770 based on a calculation by control circuit 760. For example, control circuit 760 may send a calibration control signal to sensor 770 to make a correction following an extraneous measurement detected by control circuit 760.

It should be noted that while FIGS. 7-8 provide various examples of operating epidermal electronics device 100, other steps and/or components may be used, and all such embodiments are within the scope of the present disclosure. For example, the method 810 of using epidermal electronics device 100 may include additional steps or components. Sensors 770 may produce data regarding orientation, acceleration, movement, angular motion, rotation, angular velocity, angular acceleration, and/or position or any other measured characteristic (e.g., moisture). In some embodiments, cells 120 perform the function of multiplexing sensor output. In this case, the functions of control circuit 760 may be performed by cells 120 and/or data acquisition and processing device 510. In some embodiments, the functions of data acquisition and processing device 510 are performed by control circuit 760. For example, control circuit 760 may be configured to apply algorithms to the sensor data and to estimate or calculate orientation, rotation, and/or position of attachments surface 103. In further example, method 900 of operation of an epidermal electronics device may include additional steps or components. The individual steps of method 900 may be performed simultaneously (e.g., as in pipelining). Other steps and components may be used in the methods illustrated in FIGS. 7 and 8 consistent with the disclosure made herein with regards to components and their functions and the functions of the epidermal electronics device.

Systems and methods are also described for monitoring repetitive stress injuries and arthritis. A repetitive stress injury may include damage to tendons, nerves, and other soft tissues that is caused by the repetitive and forceful physical movements or vibrations and sustained positioning of body portions in a biomechanically detrimental position, and may be characterized by numbness, pain, and a wasting and weakening of muscles. The systems and methods include generating sense signals from one or more physiological sensors and motion sensors positioned proximate to a body portion of a subject. In an embodiment, the systems and methods described herein may be used to monitor and treat a medical condition through the generation of sense signals from one or more physiological sensors and motion sensors configured to monitor one or more physiological conditions of a subject and one or more movements or positions of a body portion of the subject and to provide an effect to the body portion through action of one or more effectors. The medical condition can include, but is not limited to, a joint-based non-inflammation condition (e.g., arthralgia), a joint-based inflammation condition (e.g., arthritis), a tendon-based inflammation condition (e.g., tendonitis), a nerve entrapment or compression based condition or syndrome (e.g., carpal tunnel entrapment, cubital tunnel entrapment, tarsal tunnel entrapment, radial nerve entrapment, meralgia paresthetica). For example, carpal tunnel syndrome, a type of carpal tunnel entrapment, relates to compression of the median nerve as it passes through the carpal tunnel into the wrist, and can be related to occupational factors (see, e.g., Palmer, Best Pract Res Clin Rheumatol. February 2011; 25(1): 15-29, which is incorporated herein by reference).

In embodiments, the systems and methods described herein employ one or more physiological sensors to monitor one or more physiological conditions of a subject and to generate a sense signal in response thereto. The physiological sensors include, but are not limited to, an electromyograph, a strain sensor, a temperature sensor, an optical sensor (e.g., an LED), and an acoustic sensor.

In embodiments, the systems and methods described herein employ one or more motion sensors to monitor a movement or position of a body portion of a subject and to generate a sense signal in response thereto. The motion sensors include, but are not limited to, sensors configured to measure a repeated motion of a body portion, sensors configured to measure a number of repetitions of a movement of a body portion, sensors configured to measure a speed of a movement of a body portion, sensors configured to measure a duration of movement of a body portion, sensors configured to measure a disposition of a body portion relative to a second body portion, and sensors configured to measure an angle of movement of a body portion.

In embodiments, the systems and methods described herein employ one or more effectors to affect a body portion responsive to processing of sense signals generated by the sensor assembly. The effectors include, but are not limited to, tactile stimulators (e.g., a tactile stimulator configured to provide a tactile indication regarding a position of a body portion) and nerve stimulators (e.g., a nerve stimulator configured to provide therapeutic stimulation or electrical blockage of nerve conduction).

Figure 9:
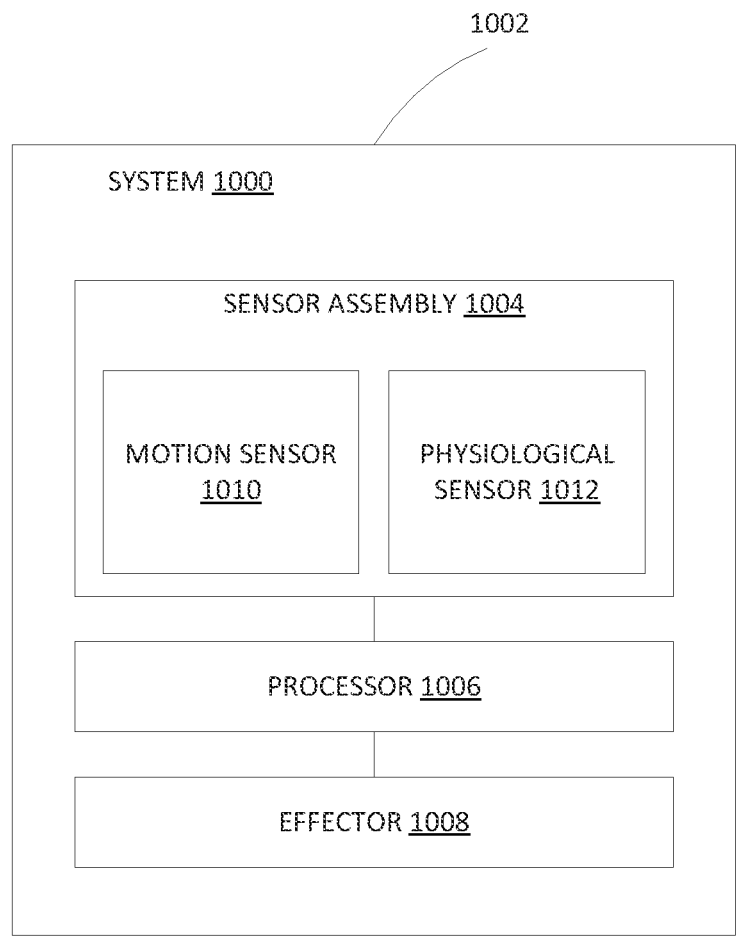
FIG. 9 is a schematic of a system for monitoring, treating, and preventing a repetitive stress injury, arthritis or other medical condition.

In an embodiment, shown in FIG. 9, a system 1000 is configured to monitor and treat a medical condition associated with a repetitive stress injury, arthritis, or other medical condition. The system 1000 includes a substrate 1002, a sensor assembly 1004, a processor 1006, and an effector 1008. In embodiments, the system 1000 includes epidermal electronic systems (EES) to monitor physiological, positional, and movement conditions for monitoring, preventing, and treating a medical condition associated with a repetitive stress injury, arthritis, or other medical condition. EES describe classes of electronic systems that provide thicknesses, effective elastic moduli, and flexibility suitable for interfacing with a skin surface (see, e.g., Kim et al., Epidermal Electronics, Science, Vol. 333, 838-843 (2011) and Yeo et al., Multifunctional Epidermal Electronics Printed Directly Onto the Skin, Advanced Materials Vol. 25(20), 2773-2778 (2013), which are incorporated herein by reference) and can incorporate sensors (e.g., physiological, temperature, strain) and associated circuitry (e.g., transistors, diodes, photodetectors, radio frequency components, capacitors, oscillators).

The substrate 1002 is a deformable (e.g., flexible, stretchable) substrate configured to interface with a skin surface of a subject. The deformable nature of the substrate 1002 facilitates interaction/interfacing with the skin surface, a generally low-modulus and deformable natural surface. For example, the substrate 1002 can include one or more of an elastomeric polymer, a hydrocolloid film, a nanomembrane (e.g., silicon nanomembrane), or other deformable material. For example, the substrate 1002 can include one or more coating. The substrate 1002 can be positioned in proximity with the skin surface according to various mechanisms including, but not limited to, affixed to the skin via an adhesive material, and held in place by an external pressure, such as pressure provided by a material wrapped around the body portion (e.g., a fabric, a garment, etc.). In embodiments, the substrate 1002 is configured to reversibly deform to coordinate with a deformation of the skin surface of the body portion upon which the substrate 1002 is mounted. In an embodiment, the substrate 1002 includes a gas-permeable elastomeric sheet on which electronic components of an EES reside (see, e.g., Kim et al., incorporated herein by reference) configured to interface with a skin surface. In an embodiment, the substrate 1002 includes a microfluidic enclosure defined by opposing structured elastomeric substrates between which electronic components of an EES reside (see e.g., Xu et al, Soft Microfluidic Assemblies of Sensors, Circuits, and Radios for the Skin, Science, Vol. 344, 70-74 (2014), which is incorporated herein by reference).

Figure 10:
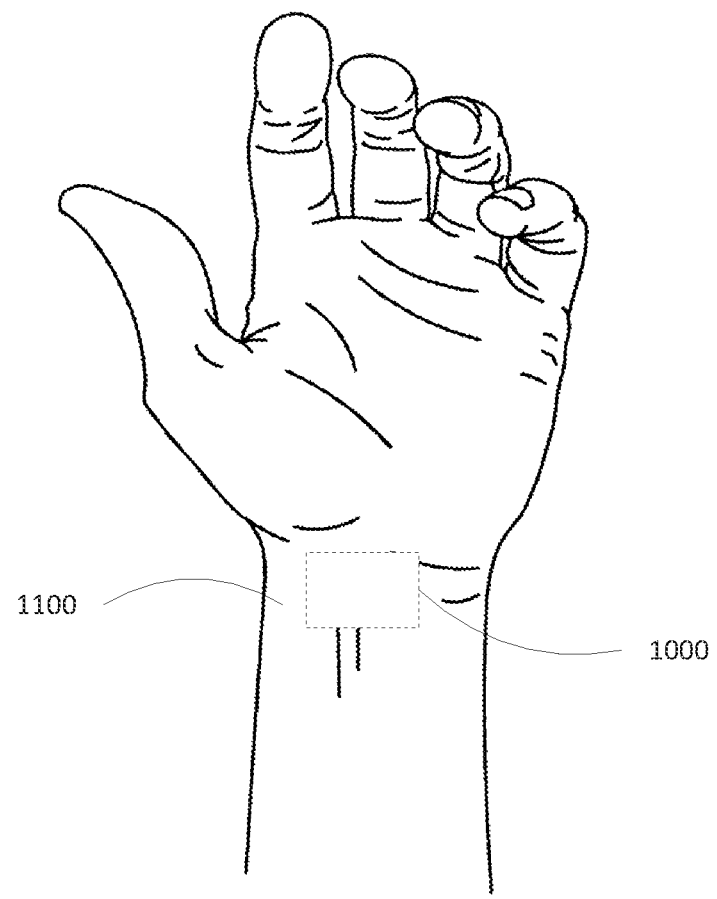
FIG. 10 is a schematic of an embodiment of a system such as shown in FIG. 9.

The substrate 1002 can also be configured for interaction with a skin surface of a particular body portion. In example embodiments, the body portion includes one or more of a finger, a hand, a wrist, a toe, a foot, an ankle, an arm, an elbow, a leg, a knee, a shoulder, a hip, a spinal portion (e.g., a region proximate to one or more of a cervical spine, a thoracic spine, a lumbar spine, a sacral spine, and a coccygeal spine), a rib portion (e.g., a region proximate to a rib, such as where the rib attaches the spine), a torso, a neck, and a head region (e.g., face, scalp). For example, the substrate 1002 can conform to a tubular structure to facilitate interaction with a finger or toe (see, e.g., Ying et al., Silicon nanomembranes for fingertip electronics, Nanotechnology, Vol. 23, No. 34, 1-7 (2012) which is incorporated herein by reference). In an embodiment, shown in FIG. 10, the system 1000 is positioned on a wrist 1100 of the subject for monitoring, preventing, and treating a medical condition associated with a repetitive stress injury, arthritis, or other medical condition associated with the wrist or other body portion in close proximity to the wrist, including, but not limited to, the hand, one or more fingers, and the arm.

Referring to FIGS. 9-14, the sensor assembly 1004 includes a motion sensor 1010 and a physiological sensor 1012. The sensor assembly 1004 is configured to generate one or more sense signals based on detection of a movement of a body portion by the motion sensor 1010 and a physiological parameter of the body portion by the physiological sensor 1012. In embodiments, the motion sensor 1010 includes one or more of an accelerometer (e.g., accelerometer 1400) and a proximity sensor (e.g., proximity sensor 1402) to detect a movement of a body portion and generate a sense signal in response thereto. The proximity sensor can include one or more of an infrared sensor (e.g., infrared sensor 1404) and an optical sensor (e.g., optical sensor 1406). In embodiments, the proximity sensor is configured to sense a second body portion proximate the body portion on which the system 1000 is positioned. For example, the system 1000 can be positioned on a wrist of a subject and the motion sensor 1010 can include a proximity sensor configured to detect one or more of a presence, a position, an angle, and a movement of another body portion proximate the wrist, such as a hand, a palm, an arm, a finger, a shoulder, and so forth. In embodiments, the proximity sensor is configured to sense a device interfacing with another portion of the skin surface or with another body portion. For example, the system 1000 can be positioned on a body portion of a subject and a second system 1000 is positioned proximate the body portion or on another body portion, where the proximity sensor of the motion sensor 1010 of the system 1000 can sense one or more of a presence, a position, an angle, and a movement of the second system 1000.

The motion sensor 1010 is configured to detect one or more of a movement of a body portion and a position of the body portion. The body portion can be the portion with which the system 1000 interfaces or can be a portion proximate the portion with which the system 1000 interfaces. In embodiments, the motion sensor 1010 generates a sense signal based on a repeated motion of the body portion. For example, the system 1000 can be positioned on a wrist of a subject and the motion sensor 1010 measures a repeated flexing or bending of the wrist, such as to move the hand or one or more fingers. In embodiments, the motion sensor 1010 measures a number of repetitions of a movement of a body portion. For example, the system 1000 can be positioned on a finger of a subject and the motion sensor 1010 measures the number of repetitions that the particular finger is flexed or bent. Measuring the number of repetitions can include, but is not limited to, measuring that zero repetitions have occurred, measuring a finite number of repetitions, measuring the number of repetitions taken over a specified time period, and determining that the number of repetitions exceeds a threshold number (e.g., a threshold at which a subject is at risk for a repetitive strain injury). In embodiments, the motion sensor 1010 measures a speed of a movement of a body portion. For example, the system 1000 can be positioned on an ankle of a subject and the motion sensor 1010 measures the speed of movement of the ankle, such as one or more of a speed of movement during a flexing of the ankle during a walking motion, a speed of movement relative to a ground surface during a walking motion, or other movement. In embodiments, the motion sensor 1010 measures a duration of a movement of a body portion. The duration can include one or more of a total duration of movement within a period of time (e.g., duration encompassing multiple repetitions of movement) and a total duration of movement for a single repetition of movement. For example, the system 1000 can be positioned on a finger of a subject and the motion sensor 1010 measures one or more of the duration of motion of bending or flexing the finger over a period of time and the duration of motion of a single repetition of movement of the finger, such as relative to the palm, hand, or wrist. The period of time over which the movement is measured can include, but is not limited to, a minute, an hour, a portion of a day during which a subject is awake and active, a day, or longer duration. In embodiments, the sensor assembly 1004 is configured to measure the disposition of the body portion over a period of time. For example, the sensor assembly 1004 may measure a disposition of the body portion over time while the body portion is one or more of at rest, while in motion, and while held in a position that is not a rest position (e.g., tensed). In embodiments, the motion sensor 1010 measures a disposition of a body portion on which the system 1000 is positioned relative to a second body portion during a movement of one or more of the body portion and the second body portion. For example, the system 1000 can be positioned on a phalange of a subject and the motion sensor 1010 measures a disposition of the phalange relative to a wrist or ankle of the subject during motion of the phalange or wrist/ankle. In embodiments, the motion sensor 1010 measures an angle of movement of a body portion. For example, the system 1000 can be positioned on an arm of a subject and the motion sensor 1010 measures an angle of movement of the arm (e.g., relative to the torso, relative to a rest position of the arm, relative to another body portion, and so forth). Measurement by the motion sensor 1010 of one or more of a repeated motion of a body portion, a number of repetitions of the movement of the body portion, a speed of the movement of the body portion, a duration of the movement of the body portion, a disposition of the body portion relative to a second body portion, and an angle of movement of the body portion provides information that can aid in the determination by the system 1000 of whether the subject has a repetitive stress injury or is at risk for a repetitive stress injury, and can provide data regarding actions to treat or avoid a particular repetitive stress injury with the system 1000.

Figure 13:
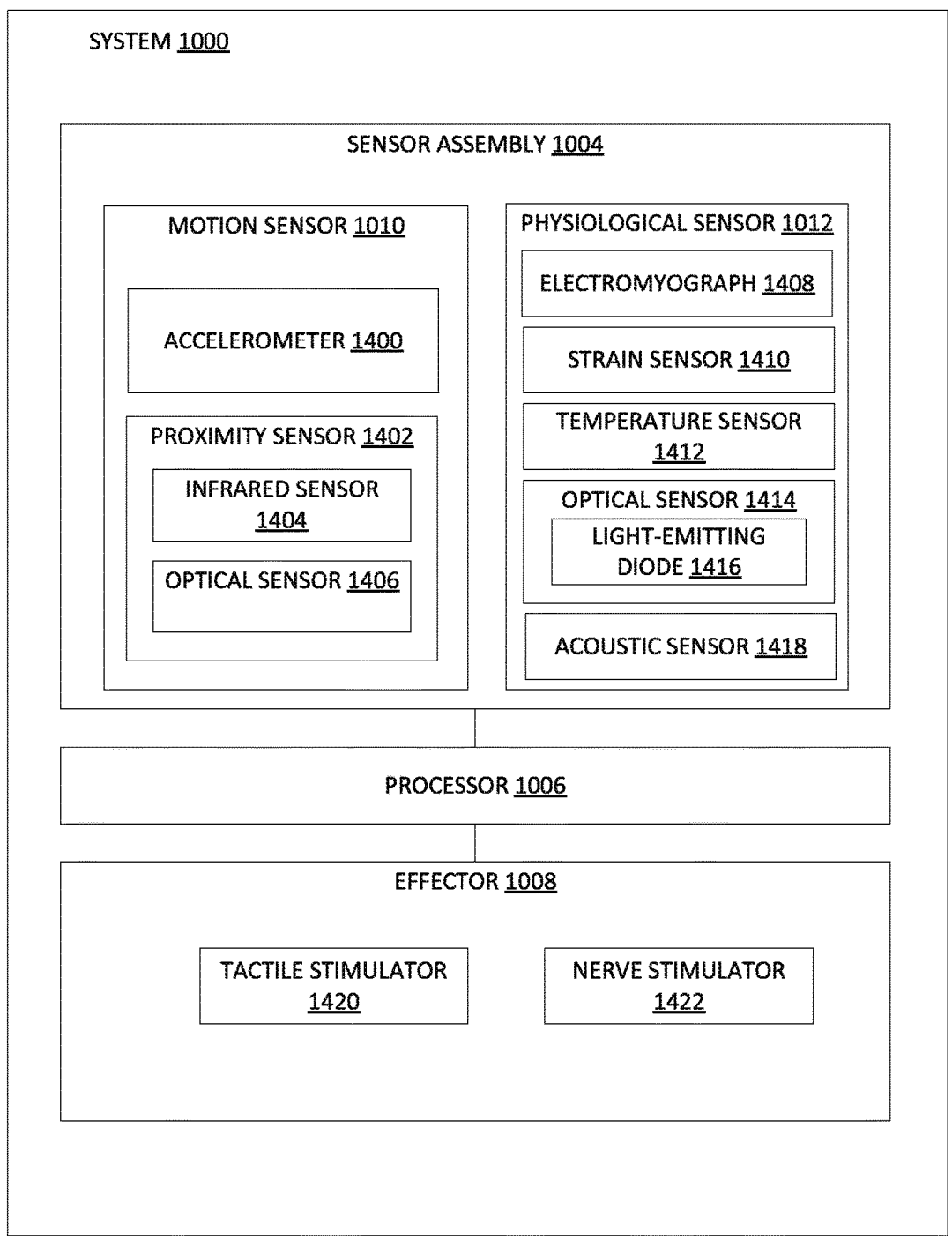
FIG. 13 is a schematic of an embodiment of a system such as shown in FIG. 9.

The physiological sensor 1012 is configured to detect a physiological parameter of the subject on which the system 1000 is positioned. In embodiments, the physiological sensor 1012 detects a localized physiological parameter provided by one or more of a body portion with which the system 1000 interfaces and a body portion proximate the portion with which the system 1000 interfaces. The physiological sensor 1012 can also be configured to detect systemic physiological parameters of the subject on which the system 1000 is positioned. In embodiments, the physiological sensor 1012 includes an electromyograph (EMG) (FIG. 13 shows electromyograph 1408), such as sensor electrodes configured to monitor the electrophysiological activity of muscle tissue proximate to the body portion on which the system 1000 is positioned. In embodiments, the physiological sensor 1012 includes a strain sensor (e.g., strain sensor 1410). For example, the strain sensor may be a silicon nanomembrane-based sensor positioned over the skin surface to measure a strain-based physiological parameter (see, e.g., Son et al., Multifunctional wearable devices for diagnosis and therapy of movement disorders, Nature Nanotechnology, Vol. 9, 397-404 (2014), which is hereby incorporated by reference). In embodiments, the physiological sensor 1012 includes a temperature sensor (e.g., temperature sensor 1412). For example, the temperature sensor can include, but is not limited to, a single point temperature sensor, a spatial imaging temperature sensor, and a microscale temperature sensor configured as a microscale heating element or actuator, such as one or more microscale temperature sensors incorporating thin serpentine features of thin metal or PIN diodes with nanoscale membranes (see, e.g., Webb et al., Ultrathin conformal devices for precise and continuous thermal characterization of human skin, Nature Materials, Vol. 12, 938-944 (2013), which is incorporated herein by reference). In embodiments, the physiological sensor 1012 includes an optical sensor (e.g., optical sensor 1414) configured to measure an optical characteristic of a body portion on which the system 1000 is positioned. For example, the optical sensor can include, but is not limited to, a light-emitting diode (LED) (e.g., light-emitting diode 1416), an LED coordinates with a photosensor, an imaging device, such as a camera, and so forth. In embodiments, the physiological sensor 1012 includes an acoustic sensor (e.g., acoustic sensor 1418). The acoustic sensor may provide data regarding motion of a joint including, but not limited to, a wrist, an elbow, a shoulder, an ankle, a knee, and a hip.

The processor 1006 is configured to receive one or more sense signals from the sensor assembly 1004 and to process the sense signals in order to provide control signals to portions of the system 1000, such as to the effector 1008. In embodiments, the processor 1006 is a resident device component that is coupled to the substrate 1002. Alternatively, the processor 1006 can be located remotely from the substrate 1002 and can send and receive signals via associated wireless communication methods including, but not limited to acoustic communication signals, optical communication signals, radio communication signals, infrared communication signals, ultrasonic communication signals, and the like.

The processor 1006 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

The effector 1008 is operably coupled to the processor 1006 and affects a body portion responsive to control by the processor 1006 to one or more of prevent and treat a medical condition associated with a repetitive stress injury, arthritis, or other medical condition. In embodiments, the effector 1008 includes one or more of a tactile stimulator (e.g., tactile stimulator 1420) and a nerve stimulator (e.g., nerve stimulator 1422). A tactile stimulator can provide a subject an indication regarding a position of a body portion. For example, the sensor assembly 1004 can generate one or more sense signals regarding a position of a body portion on which the system 1000 is positioned, where the processor 1006 receives the sense signals and instructs the effector 1008 (e.g., tactile stimulator) to provide an indication to the user regarding the position, such as by providing a vibrational response to the user. In embodiments, the processor 1006 determines that the position of the body portion is a biomechanically detrimental position. For example, the processor 1006 can compare the one or more sense signals generated by the sensor assembly 1004 to reference data indicative of a strain injury stored in a resident or remote memory device. The processor 1006 can then instruct the tactile stimulator to affect the body portion, such as by providing a vibrational effect, to provide an indication that the position of the body portion is a biomechanically detrimental position. In embodiments, the processor 1006 determines that the body portion has maintained the current position for a duration longer than a threshold duration. For example, the processor 1006 can compare the one or more sense signals generated by the sensor assembly 1004 regarding a duration of the body portion in a particular position to a threshold duration stored in a resident or remote memory device. The threshold duration can be based on biomechanical data indicative of when a repetitive stress injury is likely to occur. The processor 1006 can then instruct the tactile stimulator to affect the body portion, such as by providing a vibrational effect, to provide an indication that the body portion has maintained the current position for a duration longer than the threshold duration.

The effector 1008 can include a nerve stimulator configured to provide an electrical stimulation to one or more nerves in the subject on which the system 1000 is positioned. In embodiments, the nerve stimulator generates an electrical current or impulse to therapeutically stimulate a nerve proximate to the body portion on which the system 1000 is positioned. The therapeutic stimulation can be utilized to treat or avoid a repetitive stress injury of the subject. In embodiments, the nerve stimulator is configured to stimulate a nerve conduction of a nerve proximate to the body portion on which the system 1000 is positioned. Stimulating the nerve conduction induces movement of the body portion or sensation of the body portion. For example, the sensor assembly 1004 generates one or more sense signals based on detection of a movement or position of the body portion by the motion sensor 1010 and a physiological parameter of the body portion by the physiological sensor 1012, where the processor 1006 receives the one or more sense signals and directs the effector 1008 to affect the body portion by generating an electrical current or impulse to stimulate a nerve conduction of a nerve proximate to the body portion on which the system 1000 is positioned, such as to cause movement of the body portion or to induce a sensation of the body portion. In embodiments, the nerve stimulator is configured to stimulate the nerve conduction after a threshold period of time during which the body portion is retained in a particular position. For example, the motion sensor 1010 may provide one or more sense signals regarding the position of the body portion over a temporal duration. The system 1000 may infer that the body portion remains within a particular position when the one or more sense signals do not significantly deviate over a period of the temporal duration that corresponds to a threshold duration of time. The threshold duration of time can correspond to a time at which a body portion becomes subject to a risk of strain injury or to an increased risk of strain injury.

In embodiments, the nerve stimulator is configured to electrically block a nerve conduction of a nerve proximate to the body portion on which the system 1000 is positioned. For example, the nerve stimulator generates an electrical current or impulse to interfere with, block, alter, and the like, a nerve conduction of a nerve. Blocking the nerve conduction can inhibit a pain receptor of the subject. For example, the sensor assembly 1004 generates one or more sense signals based on detection of a movement of the body portion by the motion sensor 1010 and a physiological parameter of the body portion by the physiological sensor 1012, where the processor 1006 receives the one or more sense signals and directs the effector 1008 affect the body portion by generating an electrical current or impulse to block a nerve conduction of a nerve proximate to the body portion on which the system 1000 is positioned, such as to inhibit a pain receptor of the subject. In embodiments, the blockage of the nerve conduction can inhibit a movement of the body portion. For example, where the sensor assembly 1004 generates one or more sense signals indicating that the body portion is maintained in a biomechanically detrimental position, the processor 1006 can control the effector 1008 to block a nerve conduction of a nerve proximate to the body portion to inhibit movement of the body portion from maintaining or repositioning into the biomechanically detrimental position. Other indicators for inhibiting the movement of the body portion include, but are not limited to, repetitive movements indicative of a repetitive stress injury, maintaining the body portion in a position that exceeds a threshold duration, and the like.

Figure 11:
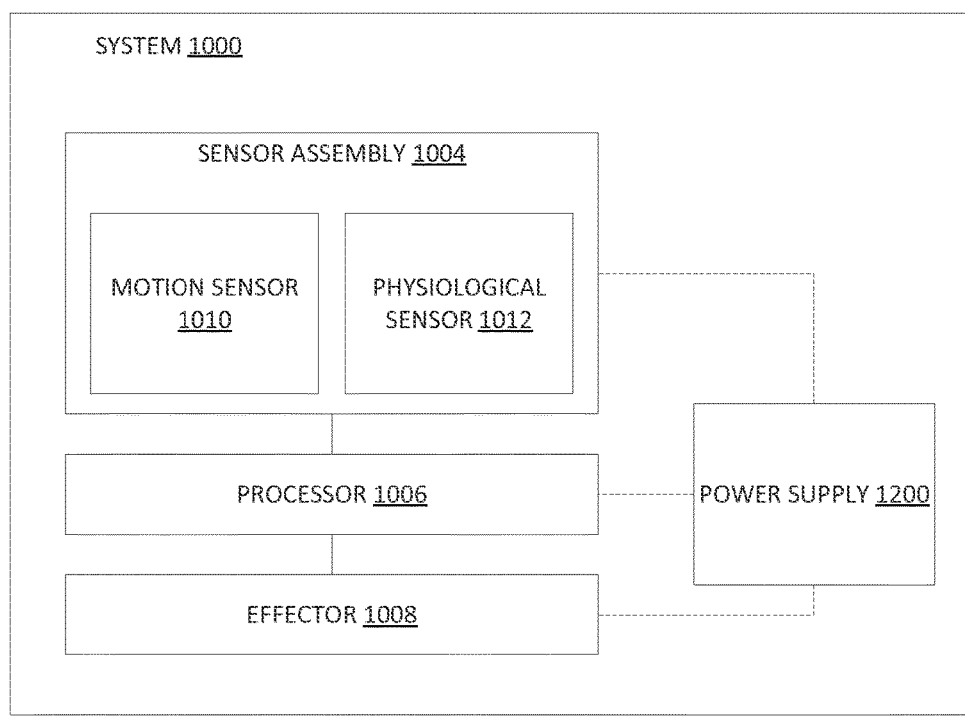
FIG. 11 is a schematic of an embodiment of a system such as shown in FIG. 9.

In embodiments, as shown in FIG. 11, the system 1000 includes a power supply 1200 configured to provide power to one or more components of the system 1000 including, but not limited to, the sensor assembly 1004, the processor 1006, and the effector 1008. In embodiments, the power supply 1200 is a resident device component that is coupled to the substrate 1002. Examples of resident device components include, but are not limited to, batteries (e.g., a thin film battery) and solar cells (e.g., silicon-based solar cells) configured to convert light energy into electrical energy for use by the components of the system 1000. In embodiments, the power supply 1200 includes one or more components positioned remotely from the substrate 1002 that transmit power signals via associated wireless power methods including, but not limited to, inductive coupling of power signals. In such embodiments, the system 1000 includes one or more components positioned on the substrate 1002 configured to one or more of receive, process, and distribute the power signals that originate from components positioned remotely from the substrate 1002. For example, the system 1000 can include a wireless power coil coupled to the substrate 1002 that is configured to receive a remote power signal, such as a remote power signal originating from a remote transmission coil (see, e.g., Kim et al., incorporated herein by reference).

Figure 12:
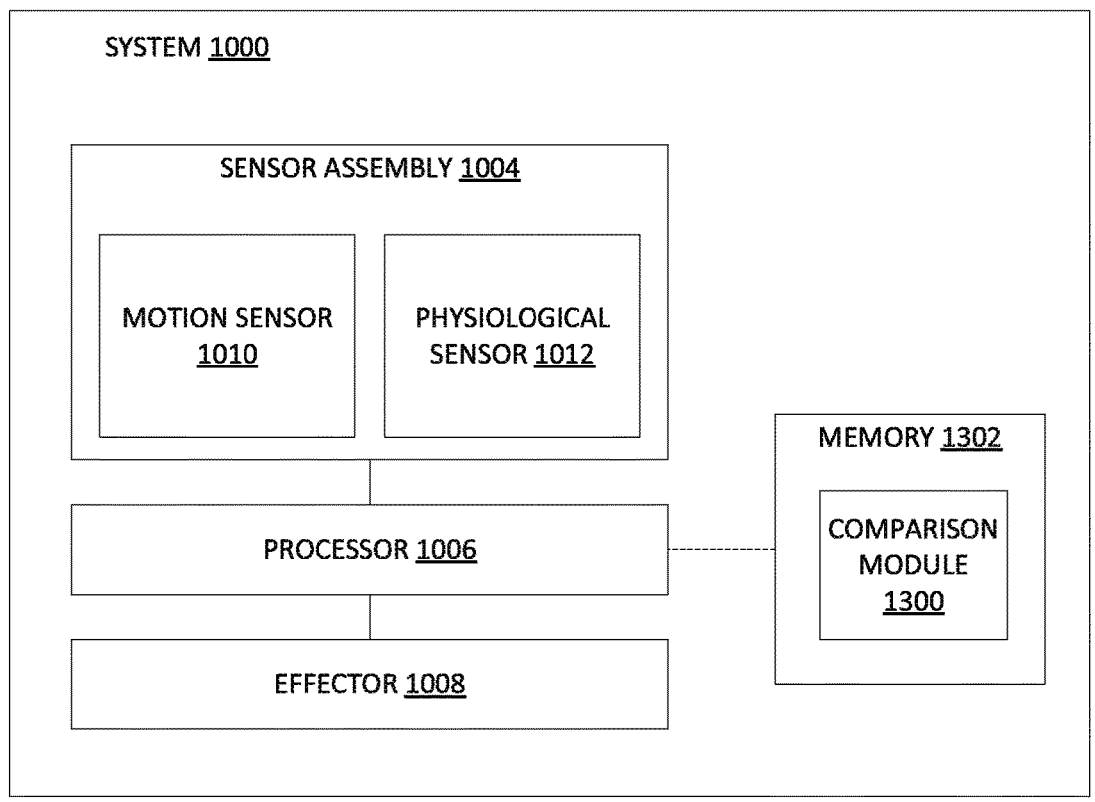
FIG. 12 is a schematic of an embodiment of a system such as shown in FIG. 9.

In embodiments, as shown in FIG. 12, the system 1000 includes a comparison module 1300 accessible by the processor 1006 to compare the movement of the body portion, detected by the motion sensor 1010 of the sensor assembly 1004, and the physiological parameter of the body portion, detected by the physiological sensor 1012 of the sensor assembly 1004, to reference data indicative of a strain injury. In embodiments, the processor 1006 accesses the comparison module 1300 by accessing a computer memory 1302, which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 1300 and which can be accessed by the processor 1006 or other accessing device. The reference data may be stored by the computer memory 1302 of the system 1000, can be accessible by the processor 1006 via wireless means, or can be available to the processor 1006 through another method. The reference data may include physiological and biomechanical information pertaining to strain injuries that include, but are not limited to, a joint-based non-inflammation condition (e.g., arthralgia), a joint-based inflammation condition (e.g., arthritis), a tendon-based inflammation condition (e.g., tendonitis), a nerve entrapment or compression based condition or syndrome (e.g., carpal tunnel entrapment, cubital tunnel entrapment, tarsal tunnel entrapment, radial nerve entrapment, meralgia paresthetica). By implementing the protocols of the comparison module 1300, the processor 1006 may compare the movement, position, and physiological data pertaining to the body portion obtained by the sensor assembly 1004 to reference data indicative of a strain injury and make a determination regarding the risk or likelihood of a strain injury occurring for the body portion. In embodiments, the processor 1006 further determines an action to be executed by the effector 1008 based upon the comparison made between the data received from the sensor assembly 1004 and the reference data. For example, where the processor 1006 determines that the body portion is at a relatively high risk for incurring a strain injury, the processor 1006 may control the effector 1008 to take a first action (e.g., electrically affect a nerve conduction), whereas if the processor 1006 determines that the body portion is at a lower risk for incurring a strain injury, the processor 1006 may control the effector 1008 to take a second action (e.g., provide a visible, audible, or tactile warning to the subject).

Figure 14:
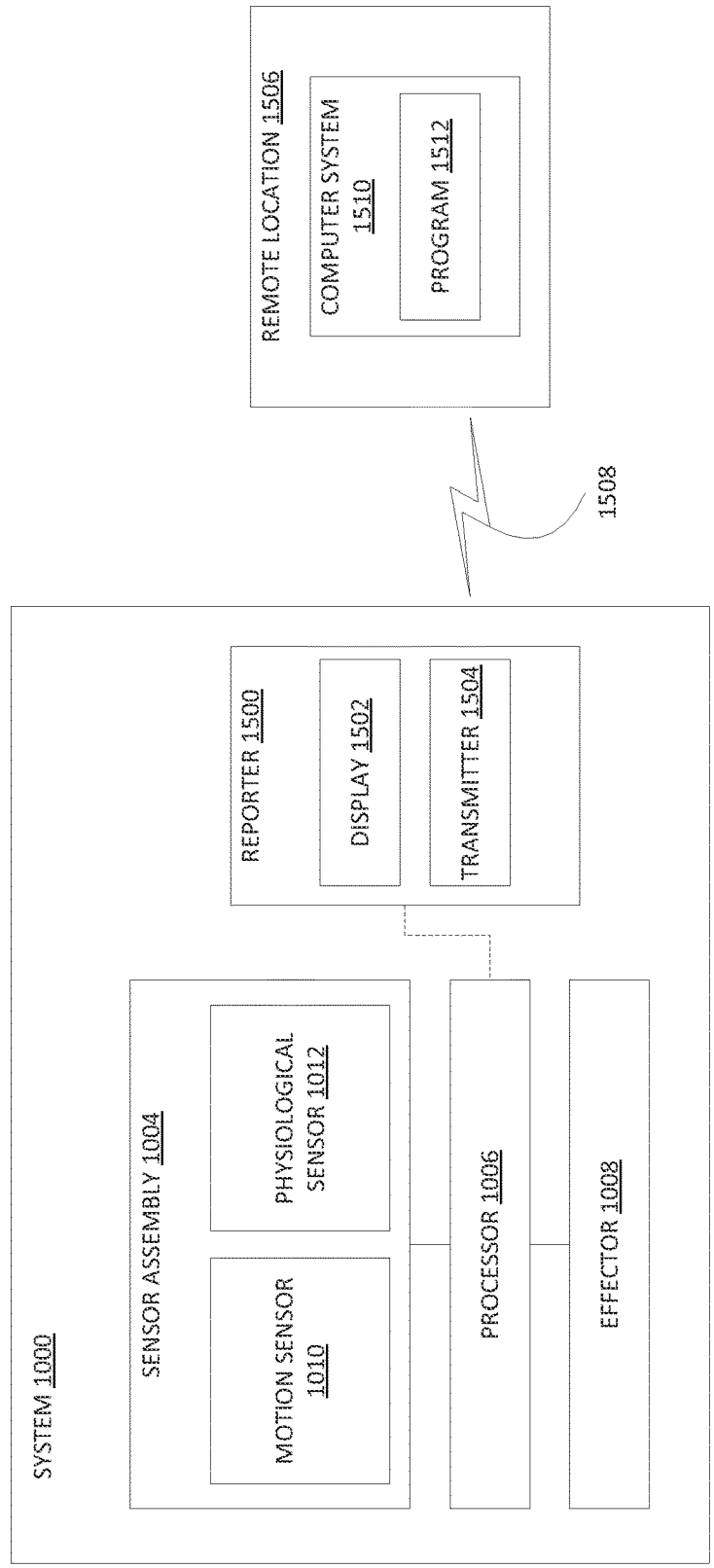
FIG. 14 is a schematic of an embodiment of a system such as shown in FIG. 9.

In embodiments, as shown in FIG. 14, the system 1000 further includes a reporter 1500 configured to convey information from the system 1000. The information from the reporter 1500 may be provided one or more of visually (e.g., visual information), audibly (e.g., auditory information), and as data (e.g., one or more data signals associated with the information to convey). In embodiments, the reporter 1500 reports one or more of an actuation of the effector 1008, a detected movement or position of the body portion, and a detected physiological condition. The reporter 1500 can provide warnings or instructions regarding the movement, position, and the physiological condition of the body portion. For example, the reporter 1500 may be configured to report a warning of a risk of a biomechanically detrimental positioning of the body portion. The biomechanically detrimental positioning may influence the risk for a repetitive strain injury (e.g., as determined by the processor 1006 implementing the comparison module 1300). In embodiments, the reporter 1500 is configured to report an instruction to move the body portion. The reporter 1500 may function in combination with the effector 1008 to provide visual or auditory context to the subject upon action of the effector 1008, such as when a tactile stimulation occurs via a tactile stimulator of the effector 1008. In embodiments, the reporter 1500 includes a display 1502 configured to report, communicate, or otherwise provide information to the subject utilizing the system 1000. The display 1502 may include, but is not limited to, a graphical user interface (GUI), a touchscreen assembly (e.g., a capacitive touch screen), a liquid crystal display (LCD), a light-emitting diode (LED) display, and a projection-based display. In embodiments, the reporter 1500 includes a transmitter 1504 configured to transmit information from the system 1000 to a remote location 1506 (e.g., a remote entity, a remote device, and so forth). In embodiments, the remote location includes a communication device, such as one or more of a mobile communication device and a computer system including, but not limited to, mobile computing devices (e.g., hand-held portable computers, Personal Digital Assistants (PDAs), laptop computers, netbook computers, tablet computers, and so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The reporter 1500 can communicate (e.g., send and receive communication signals) with the remote location 1506 via one or more connected and wireless communication mechanisms (FIG. 14 displays a wireless communication mechanism 1508) including, but not limited to acoustic communication signals, optical communication signals, radio communication signals, infrared communication signals, ultrasonic communication signals, and the like.

In embodiments, the remote location 1506 includes a computer system configured to store and execute one or more computer-executable programs, whereby the reporter can interact with (e.g., remotely access, execute, and so forth) and modify the programs stored on the computer system. For example, FIG. 14 displays the remote location 1506 including a computer system 610 having a computer-executable program 612 stored thereon. In embodiments, the information provided to the computer system 610 by the reporter 1500 is used to populate fields of the program, such as fields associated with risks of repetitive stress injury. In embodiments, the program 612 includes scheduling software configured to provide personnel scheduling functionality, such as to schedule personnel to particular tasks within an organizational structure while considering the risks for repetitive stress injuries associated with the various tasks engaged by the personnel and including actual data, provided by the reporter 1500, of actual risks of repetitive stress injuries of individuals interfacing with the system 1000. For example, the scheduling software can include instructions that, when executed by a computer processor on the computer system 610, causes the computer system 610 to provide real-time personnel scheduling. The reporter 1500 can provide information associated with risks for repetitive stress injuries for one or more individuals interfacing with the system 1000 based on measured movements, positions, and physiological conditions in order for the program 612 to make real-time personnel scheduling assignments, such as to make substantially instantaneous or real-time determinations of personnel assignments to minimize the risk of repetitive stress injuries on an individual basis, an organizational basis, and so forth.

As another example, the scheduling software can include instructions, that when executed by a computer processor on the computer system 610, causes the computer system 610 to provide long-term personnel scheduling. The reporter 1500 can provide information associated with risks for repetitive stress injuries for one or more individuals interfacing with the system 1000 based on measured movements, positions, and physiological conditions in order for the program 612 to make long-term personnel scheduling assignments, such as to make determinations of personnel assignments over time to minimize the risk of repetitive stress injuries on an individual basis, an organizational basis, and so forth.

As another example, the scheduling software can include instructions, that when executed by a computer processor on the computer system 610, causes the computer system 610 to provide personnel tracking. The reporter 1500 can provide information associated with risks for repetitive stress injuries for one or more individuals interfacing with the system 1000 based on measured movements, positions, and physiological conditions in order for the program 612 to track the risks of repetitive stress injuries associated with particular individuals, which can be coordinated with the tracking of the particular assignments of the individual, such as to make determinations of risks of repetitive stress injuries for the individual based on the particular assignments handled by the individual. The information provided by the reporter 1500 can be used to track an individual's propensity for risk of repetitive stress injury as compared to a group of individuals, such as to determine whether the particular individual engages in more biomechanically detrimental activities than the group, to determine whether the particular individual engages in more biomechanically detrimental positioning than the group (e.g., the individual has improper form for performing the various tasks associated with specific job assignments), and so forth.

Figure 15A:
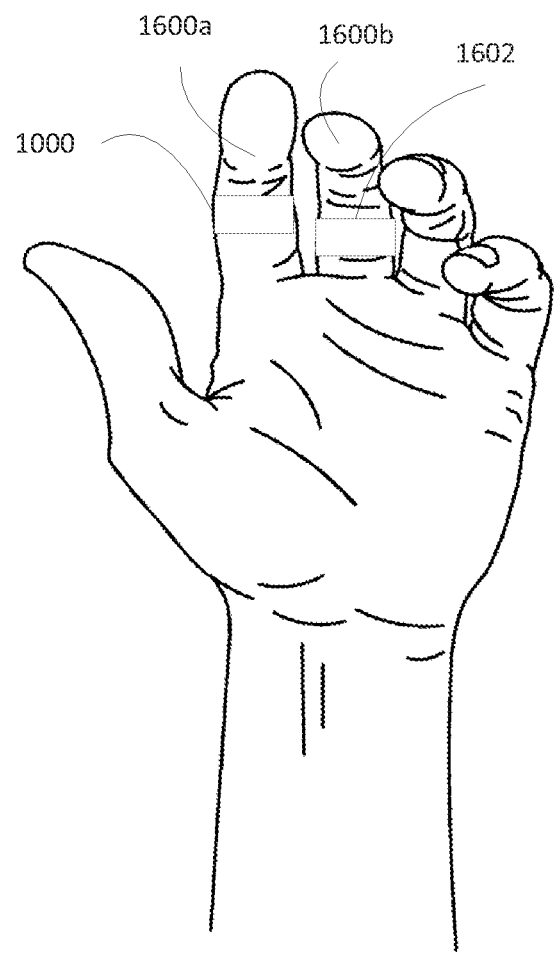
FIG. 15A is a schematic of an embodiment of a system such as shown in FIG. 9.

FIG. 15A illustrates an example environment in which embodiments of the system 1000 may be implemented. As shown, the system 1000 is positioned on a finger 1600a of a subject. In embodiments, the system 1000 further includes a second device configured to generate one or more sense signals based on detected movements, positions, and physiological parameters of the body portion on which the second device is positioned. The second device can then affect the body portion on which it is positioned, as described herein with respect to the effector 1008 of the system 1000. For example, as shown in FIG. 15A, the system 1000 includes a second device 1602 positioned on another finger 1600b of the same hand of the subject, although other positional configurations can be utilized, including but not limited to, positioning the second device 1602 on a different portion of the same finger 1600a, or positioning the second device 1602 on a hand, a wrist, a toe, a foot, an ankle, an arm, an elbow, a leg, a knee, a shoulder, a hip, a spinal portion (e.g., a region proximate to one or more of a cervical spine, a thoracic spine, a lumbar spine, a sacral spine, and a coccygeal spine), a rib portion (e.g., a region proximate to a rib, such as where the rib attaches the spine), a torso, a neck, and a head region (e.g., face, scalp).

Figure 15B:
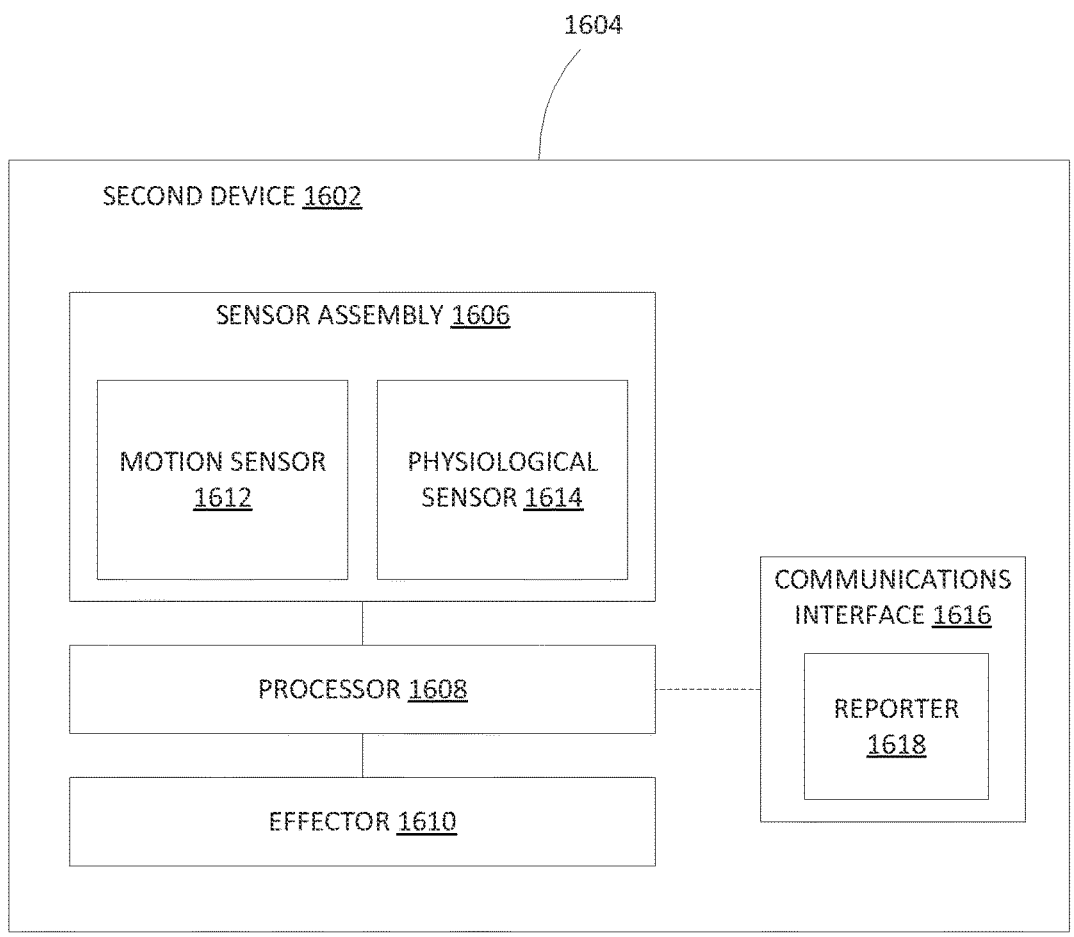
FIG. 15B is a schematic of an embodiment of a system such as shown in FIG. 9.

In embodiments, an example of which is shown in FIG. 15B, the second device 1602 includes a deformable substrate 1604, a sensor assembly 1606, a processor 1608, and an effector 1610. The second device 1602 incorporates epidermal electronic systems (EES) to monitor physiological, positional, and movement conditions for monitoring, preventing, and treating a medical condition associated with a repetitive stress injury, arthritis, or other medical condition. The deformable substrate 1604 is a deformable (e.g., flexible, stretchable) substrate configured to interface with a skin surface of a subject. The deformable nature of the substrate 1604 facilitates interaction/interfacing with the skin surface, a generally low-modulus and deformable natural surface. In embodiments, the structure of the substrate 1604 is similar to, or the same as, the structure of the substrate 1002 described herein, with corresponding functionalities.

As shown in FIG. 15B, the sensor assembly 1606 of the second device 1602 includes a motion sensor 1612 and a physiological sensor 1614. The sensor assembly 1606 is configured to generate one or more sense signals based on detection of a movement or position of a body portion by the motion sensor 1612 and a physiological parameter of the body portion by the physiological sensor 1614. In embodiments, the structures of the sensor assembly 1606, the motion sensor 1612, and the physiological sensor 1614 are similar to, or the same as, the structures of the sensor assembly 1004, the motion sensor 1010, and the physiological sensor 1012, respectively, described herein, including but not limited to, accelerometers, proximity sensors, electromyographs (EMG), strain sensors, temperature sensors, optical sensors, and acoustic sensors, with corresponding functionalities.

The processor 1608 is configured to receive one or more sense signals from the sensor assembly 1606 and to process the sense signals in order to provide control signals to portions of the second device 1602, such as to the effector 1610. In embodiments, the structure of the processor 1608 is similar to, or the same as, the structure of the processor 1006 described herein, with corresponding functionalities.

The effector 1610 is operably coupled to the processor 1608 and affects a body portion responsive to control by the processor 1608 to one or more of prevent and treat a medical condition associated with a repetitive stress injury, arthritis, or other medical condition. For example, the effector 1610 affects the finger 1600b under the control of the processor 1608, based on the processing of the one or more sense signals from the sensor assembly 1606. In embodiments, the structure of the effector 1610 is similar to, or the same as, the structure of the effector 1008 described herein, including but not limited to, tactile stimulators and nerve stimulators, with corresponding functionalities.

In embodiments, one or more components of the system 1000 interact with the second device 1602. One or more components of the system 1000 and the second device 1602 are configured to detect the presence of the respective other of the components of the system 1000 and the second device 1602. For example, the motion sensor 1010 of the system 1000 may sense one or more properties of the second device 1602 to detect a presence of the second device on the finger 1600b, and the motion sensor 1612 of the second device 1602 may sense one or more properties of the system 1000, such as the presence of the substrate 1002 positioned on the finger 1600a, to detect a presence of the system 1000. In embodiments, the motion sensor 1010 of the system 1000 may sense one or more properties of the finger 1600b to detect one or more of the presence of the finger 1600b, the proximity of the finger 1600b relative to the finger 1600a, and the disposition of the finger 1600b relative to the finger 1600a. In embodiments, the motion sensor 1612 of the second device may sense one or more properties of the finger 1600a to detect one or more of the presence of the finger 1600a, the proximity of the finger 1600a relative to the finger 1600b, and the disposition of the finger 1600a relative to the finger 1600b.

In embodiments, as shown in FIG. 15B, the second device 1602 includes a communications interface 1616 to send communication signals from the second device 1602 and to receive communication signals from a remote location or device via one or more connected (e.g., wired connections) and wireless communication mechanisms including, but not limited to acoustic communication signals, optical communication signals, radio communication signals, infrared communication signals, ultrasonic communication signals, and the like. FIG. 15B shows an embodiment where the communications interface 1616 includes a reporter 1618 configured to convey information from the second device 1602. The information from the reporter 1618 may be provided one or more of visually (e.g., visual information), audibly (e.g., auditory information), and as data (e.g., one or more data signals associated with the information to convey). In embodiments, the structure and functionality of the reporter 1618 is similar to, or the same as, the structure and functionalities of the reporter 1500 described herein.

In embodiments, the communications interface 1616 of the second device 1602 facilitates communication and interaction between the second device 1602 and other components of the system 1000, including but not limited to, the processor 1006 and the reporter 1500. Accordingly, the communications interface 1616 facilitates the transfer of data between the second device 1602 and other components of the system 1000. The data can include, but is not limited to, data associated with one or more of an actuation of an effector (e.g., effector 1008, effector 1610), a detected movement or position of the body portion (e.g., sensed by motion sensor 1010, motion sensor 1612), a detected physiological condition (sensed by physiological sensor 1012, physiological sensor 1614), warnings or instructions regarding the movement, position, and the physiological condition of the body portion, an indication that warnings or instructions regarding the movement, position, and the physiological condition of the body portion have been reported, a position of a body portion relative to another body portion, and a position of the second device 1602 relative to the position of one or more components of the system 1000.

Figure 16:
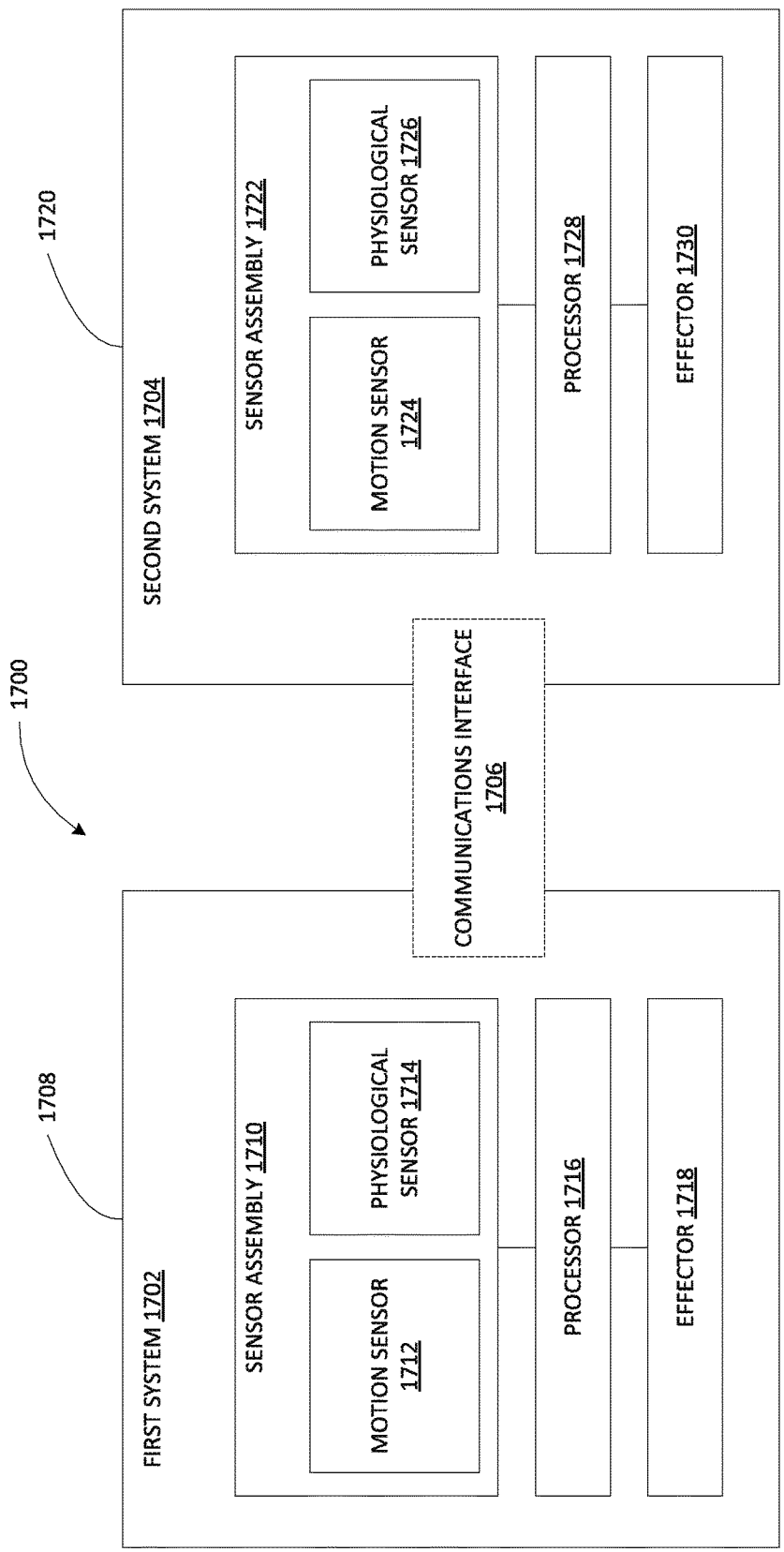
FIG. 16 is a schematic of a system for monitoring, treating, and preventing a repetitive stress injury, arthritis or other medical condition.

Referring now to FIG. 16, an example environment 1700 in which embodiments may be implemented is shown. The environment 1700 includes a first system 1702, a second system 1704, and a communications interface 1706 coupled between the first system 1702 and the second system 1704. The first system 1702 and the second system 1704 are configured to monitor, prevent, and treat a medical condition associated with a repetitive stress injury, arthritis, or other medical condition, and employ epidermal electronic systems (EES) to monitor physiological, positional, and movement conditions for monitoring, preventing, and treating a medical condition associated with a repetitive stress injury, arthritis, or other medical condition. The communications interface 1706 facilitates the transfer of one or more communication signals between the first system 1702 and the second system 1704. As shown, the first system 1702 includes a deformable substrate 1708 configured for interaction with a skin surface of a particular body portion, a sensor assembly 1710 including a motion sensor 1712 and a physiological sensor 1714 configured to generate one or more sense signals based on detection of a movement of a body portion by the motion sensor 1712 and a physiological parameter of the body portion by the physiological sensor 1714, a processor 1716 configured to receive one or more sense signals from the sensor assembly 1710 and to process the sense signals in order to provide control signals to portions of the first system 1702, and an effector 1718 operably coupled to the processor 816 to affect a body portion responsive to control by the processor 1716 to one or more of prevent and treat a medical condition associated with a repetitive stress injury, arthritis, or other medical condition. The substrate 1708, the sensor assembly 1710, the processor 1716, and the effector 1718 may correspond to the substrate 1002, the sensor assembly 1004, the processor 1006, and the effector 1008, respectively. The second system 1704 includes a deformable substrate 1720 configured for interaction with a skin surface of a particular body portion, a sensor assembly 1722 including a motion sensor 1724 and a physiological sensor 1726 configured to generate one or more sense signals based on detection of a movement of a body portion by the motion sensor 1724 and a physiological parameter of the body portion by the physiological sensor 1726, a processor 1728 configured to receive one or more sense signals from the sensor assembly 1722 and to process the sense signals in order to provide control signals to portions of the second system 1704, and an effector 1730 operably coupled to the processor 1728 to affect a body portion responsive to control by the processor 1728 to one or more of prevent and treat a medical condition associated with a repetitive stress injury, arthritis, or other medical condition. The substrate 1720, the sensor assembly 1722, the processor 1728, and the effector 1730 may correspond to the substrate 1604, the sensor assembly 1606, the processor 1608, and the effector 1610, respectively. The communications interface 1706 facilitates communication between the first system 1702 and the second system 1704 and may facilitate communication from one or more of the first system 1702 and the second system 1704 with a remote device or location. In embodiments, the communications interface 1706 includes a reporter associated with one or more of the first system 1702 and the second system 1706, such as described with reference to the reporter 1500 and the reporter 1618. In embodiments, the example environment 1700 includes a power supply in power communication with one or more of the first system 1702, the second system 1704, and the communications interface 1706. For example, a power supply may be positioned remotely from the first system 1702, the second system 1704, and the communications interface 1706 and provide one or more wireless power signals to the first system 1702, the second system 1704, and the communications interface 1706.

Figure 17:
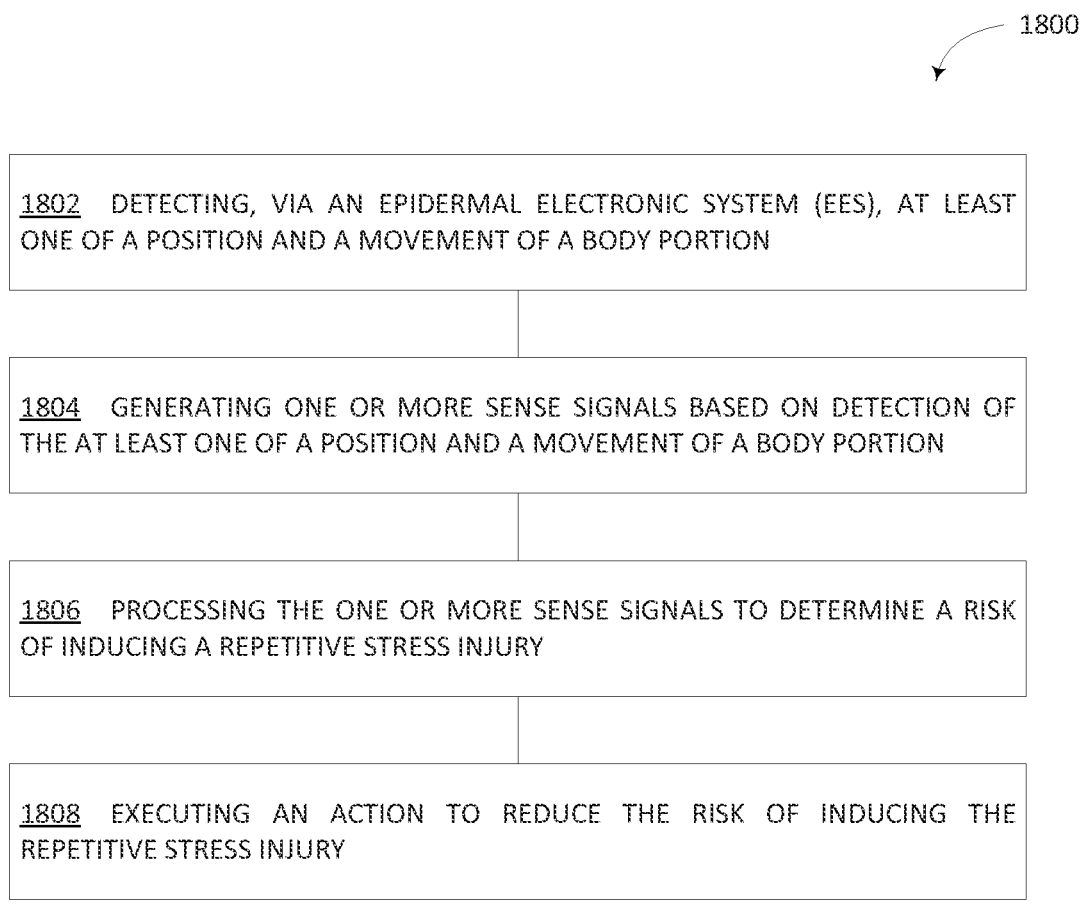
FIG. 17 is a flowchart of a method of monitoring, preventing, and treating a medical condition associated with a repetitive stress injury, arthritis, or other medical condition.

FIG. 17 illustrates a method 1800 for monitoring, preventing, and treating a medical condition associated with a repetitive stress injury, arthritis, or other medical condition. Method 1800 shows detecting, via an epidermal electronic system (EES), at least one of a position and a movement of a body portion in block 1802. For example, the motion sensor 1010 provided on an EES-based system, such as system 1000, can detect at least one of a position and a movement of a body portion, as described herein. Method 1800 also includes generating one or more sense signals based on detection of the at least one of a position and a movement of a body portion in block 1804. For example, the motion sensor 1010 can generate one or more sense signals based on detecting at least one of a position and a movement of a body portion, as described herein. Method 1800 further includes processing the one or more sense signals to determine a risk of inducing a repetitive stress injury in block 1806. For example, the processor 1006 can receive the one or more sense signals generated from the motion sensor 1010 of the sensor assembly 1004, and can process the one or more sense signals to determine a risk of inducing a repetitive stress injury, such as by accessing and executing the comparison module 1300, as described herein. Method 1800 further includes executing an action to reduce the risk of inducing the repetitive stress injury in block 1808. For example, the processor 1006 can provide one or more control signals to the effector 1008 to affect the body portion to reduce the risk of inducing the repetitive stress injury, as described herein.

FIG. 18 depicts further aspects of the method 1800 illustrated in FIG. 17. Block 1806 shows processing the one or more sense signals to determine a risk of inducing a repetitive stress injury and includes optional block 1900 that shows comparing the one or more sense signals to reference data indicative of a strain injury to determine the risk of inducing the strain injury. For example, the processor 1006 can access and execute the comparison module 1300 to compare the one or more sense signals generated by the sensor assembly 1004 to reference data indicative of a strain injury. Block 1900 also includes optional block 1902 that shows determining the action to execute based upon comparing the one or more sense signals to reference data indicative of a strain injury. For example, the processor 1006 can determine which action for the effector 1008 to take based on a comparison of the one or more sense signals to reference data indicative of a strain injury: where immediate action is warranted, the processor 1006 may determine to stimulate a nerve conduction via the effector 1008 to induce movement of the body portion; where the risk of the repetitive stress injury is lesser, the processor 1006 may determine to provide a tactile simulation via the effector 1008.

FIG. 19 depicts further aspects of the method 1800 illustrated in FIG. 17. Block 1806 shows executing an action to reduce the risk of inducing the repetitive stress injury and includes optional block 2000 that shows reporting the determination of the risk of inducing the repetitive strain injury to reduce the risk. Block 2000 includes optional block 2002 that shows providing a tactile indication of the risk. Block 2002 includes optional block 2004, which shows providing a vibration-based indication of the risk and optional block 2006, which shows providing a tactile indication regarding a position of the body portion. Block 2006 includes optional block 2008, which shows providing a tactile indication that the position is a biomechanically detrimental position, and block 2010, which shows providing a tactile indication that the body portion has been in the position longer than a threshold duration.

FIG. 20 depicts further aspects of the method 1800 illustrated in FIG. 19. Block 1806 shows executing an action to reduce the risk of inducing the repetitive stress injury and includes optional block 2000 that shows reporting the determination of the risk of inducing the repetitive strain injury to reduce the risk. Block 2000 includes optional block 2100 that shows providing a visual indication of the risk. Block 2100 includes optional block 2102 that shows providing a visual indication regarding a position of the body portion. Block 2102 includes optional block 2104, which shows providing a visual indication that the position is a biomechanically detrimental position, and optional block 2106, which shows providing a visual indication that the body portion has been in the position longer than a threshold duration.

FIG. 21 depicts further aspects of the method 1800 illustrated in FIG. 19. Block 1806 shows executing an action to reduce the risk of inducing the repetitive stress injury and includes optional block 2000 that shows reporting the determination of the risk of inducing the repetitive strain injury to reduce the risk. Block 2000 includes optional block 2200 that shows providing an auditory indication of the risk. Block 2200 includes optional block 2202 that shows providing an auditory indication regarding a position of the body portion. Block 2202 includes optional block 2204, which shows providing an auditory indication that the position is a biomechanically detrimental position, and optional block 2206, which shows providing an auditory indication that the body portion has been in the position longer than a threshold duration.

FIG. 22 depicts further aspects of the method 1800 illustrated in FIG. 19. Block 1806 shows executing an action to reduce the risk of inducing the repetitive stress injury and includes optional block 2000 that shows reporting the determination of the risk of inducing the repetitive strain injury to reduce the risk. Block 2000 includes optional blocks 2300, 2302, 2304, and 2306. Block 2300 shows reporting at least one of an actuation of an effector configured to execute the action, a detected movement of the body portion, or a detected physiological condition. Block 2302 shows providing a warning of a risk of a biomechanically detrimental positioning of the body portion. Block 2304 shows providing an instruction to move the body portion. Block 2306 shows communicating the determination to a remote location and includes optional block 2308, which shows interacting with a program stored on the computer system, and optional block 2310, which shows modifying a program stored on the computer system.

FIG. 23 depicts further aspects of the method 1800 illustrated in FIG. 17. Block 1808 shows executing an action to reduce the risk of inducing the repetitive stress injury and includes optional block 2400 that shows stimulating a nerve proximate to the body portion. Block 2400 includes optional block 2402 that shows inducing at least one of a movement or a sensation of the body portion by stimulating the nerve conduction of the nerve proximate to the body portion. Block 2402 includes optional block 2404 that shows inducing at least one of a movement or a sensation of the body portion by stimulating a nerve conduction of the nerve after a threshold period of time during which the body portion is retained in a particular position.

FIG. 24 depicts further aspects of the method 1800 illustrated in FIG. 17. Block 1808 shows executing an action to reduce the risk of inducing the repetitive stress injury and includes optional block 2500 that shows electrically blocking a nerve conduction of a nerve proximate to the body portion. Block 2500 includes optional block 2502, which shows electrically blocking a nerve conduction of a nerve proximate to the body portion to inhibit a pain receptor, and optional block 2504, which shows electrically blocking a nerve conduction of a nerve proximate to the body portion to inhibit a movement of the body portion.

FIG. 25 depicts further aspects of the method 1800 illustrated in FIG. 17. Block 1802 shows detecting, via an epidermal electronic system (EES), at least one of a position and a movement of a body portion and includes optional blocks 2600, 2602, 2604, 2606, 2608, and 2610. Block 2600 shows measuring, via an epidermal electronic system (EES), a repeated motion of the body portion. Block 2602 shows measuring, via an epidermal electronic system (EES), a number of repetitions of the movement of the body portion. Block 2604 shows measuring, via an epidermal electronic system (EES), a speed of the movement of the body portion. Block 2606 shows measuring, via an epidermal electronic system (EES), a duration of the movement of the body portion. Block 2608 shows measuring, via an epidermal electronic system (EES), a disposition of the body portion relative to a second body portion. Block 2610 shows measuring, via an epidermal electronic system (EES), an angle of movement of the body portion.

FIG. 26 depicts further aspects of the method 1800 illustrated in FIG. 17 and includes optional block 2700, which shows detecting, via an epidermal electronic system (EES), a physiological parameter of the body portion, and optional block 2702, which shows generating one or more sense signals based on detection of the physiological parameter of the body portion.

FIG. 27 depicts further aspects of the method 1800 illustrated in FIG. 26. Block 2700 shows detecting, via an epidermal electronic system (EES), a physiological parameter of the body portion and includes optional blocks 2800, 2802, 2804, 2806, and 2808. Block 2800 shows detecting a temperature of the body portion. Block 2802 shows detecting a strain of the body portion. Block 2804 shows detecting a blood flow of the body portion. Block 2806 shows detecting a blood oxygenation level of the body portion. Block 2808 shows detecting an electrical activity of the body portion.

FIG. 28 depicts further aspects of the method 1800 illustrated in FIG. 17 and includes optional block 2900, which shows detecting, via an epidermal electronic system (EES), a disposition of the body portion. Block 2900 includes optional block 2902, which shows detecting, via an epidermal electronic system (EES), an angle of a joint proximate the body portion, and optional block 2904, which shows detecting, via an epidermal electronic system (EES), a disposition of the body portion over a period of time.

FIG. 29 depicts further aspects of the method 1800 illustrated in FIG. 17 and includes optional block 3000, which shows detecting, via an epidermal electronic system (EES), a device interfacing with at least one of the body portion and another body portion, and optional block 3002, which shows transmitting a communication signal to the device. Block 3002 includes optional block 3004 that shows transmitting the one or more sense signals generated based on detection of at least one of the position and the movement of the body portion to the device.

FIG. 30 depicts further aspects of the method 1800 illustrated in FIG. 17 and includes optional block 3100, which shows detecting, via an epidermal electronic system (EES), at least one of a position and a movement of a second body portion proximate the body portion.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
a first system including:
a deformable substrate configured to interface with a skin surface of a first body portion;
a sensor assembly coupled to the deformable substrate, the sensor assembly including a motion sensor and a physiological sensor, the motion sensor including a proximity sensor configured to detect a movement of the first body portion relative to a second body portion proximate the first body portion, the sensor assembly configured to generate one or more sense signals based on detection of the movement of the first body portion relative to the second body portion by the proximity sensor and a physiological parameter of the first body portion by the physiological sensor;
a processor operably coupled to the sensor assembly and configured to receive the one or more sense signals, the processor configured to compare the one or more sense signals to a threshold duration and to determine whether the first body portion is held in a position for a duration longer than the threshold duration; and
an effector operably coupled to the processor and configured to affect the first body portion responsive to control by the processor, the effector including a nerve stimulator configured to affect a nerve proximate to the first body portion responsive to control by the processor when the first body portion is determined to be held in the position for the duration longer than the threshold duration;
a second system including:
a second deformable substrate configured to interface with a second skin surface;
a second sensor assembly coupled to the second deformable substrate, the second sensor assembly including a second motion sensor and a second physiological sensor, the second sensor assembly configured to generate one or more sense signals based on detection of a movement of a third body portion by the second motion sensor of the second sensor assembly and a physiological parameter of the third body portion by the second physiological sensor of the second sensor assembly;
a second processor operably coupled to the second sensor assembly and configured to receive the one or more sense signals of the second sensor assembly; and
a second effector operably coupled to the second processor and configured to affect the third body portion responsive to control by the second processor; and
a communications interface between the first system and the second system, wherein the first system and the second system are configured to provide one or more communication signals to the respective other of the first system and the second system via the communications interface.

2. The system of claim 1, wherein the second effector is a nerve stimulator.

3. The system of claim 1, wherein the nerve stimulator is configured to therapeutically stimulate the nerve proximate to the first body portion.

4. The system of claim 3, wherein the nerve stimulator is configured to stimulate a nerve conduction of the nerve to induce at least one of a movement or a sensation of the first body portion.

5. The system of claim 1, wherein the nerve stimulator is configured to electrically block a nerve conduction of the nerve proximate to the first body portion.

6. The system of claim 1, wherein the communications interface includes a reporter.

7. The system of claim 6, wherein the reporter is configured to report at least one of an actuation of at least one of the effector and the second effector, a detected movement of at least one of the first body portion and the third body portion, and a detected physiological condition.

8. The system of claim 6, wherein the reporter includes a transmitter configured to transmit data to a remote location.

9. The system of claim 1, wherein one or more of the first system and the second system further includes a power supply, the power supply including at least one of a battery coupled to the deformable substrate or to the second deformable substrate, a thin film battery coupled to the deformable substrate or to the second deformable substrate, a wireless power coil configured to receive a remote power signal, an inductive coil configured to receive a remote power signal from a transmission coil, and a solar cell coupled to the deformable substrate or to the second deformable substrate.

10. The system of claim 1, wherein at least one of the motion sensor and the second motion sensor is configured to measure at least one of a repeated motion of at least one of the first body portion and the third body portion, a number of repetitions of the movement of at least one of the first body portion and the third body portion, a speed of the movement of at least one of the first body portion and the third body portion, a duration of the movement of at least one of the first body portion and the third body portion, a disposition of the first body portion relative to a third body portion, and an angle of movement of at least one of the first body portion and the third body portion.

11. The system of claim 1, wherein at least one of the physiological sensor and the second physiological sensor includes at least one of an electromyograph (EMG), a strain sensor, a temperature sensor, an optical sensor, a light emitting diode (LED), and an acoustic sensor.

* * * * *